(12) United States Patent
Vergnolle et al.

(10) Patent No.: US 9,688,742 B2
(45) Date of Patent: Jun. 27, 2017

(54) RECOMBINANT PROBIOTIC BACTERIA FOR THE PREVENTION AND TREATMENT OF INFLAMMATORY BOWEL DISEASE (IBD) AND IRRITABLE BOWEL SYNDROME (IBS)

(71) Applicants: INSTITUT NATIONAL DE LA SANTE ET DE LA RECHERCHE MEDICALE, Paris (FR); INSTITUT NATIONAL DE LA RECHERCHE AGRONOMIQUE (INRA), Paris (FR); UNIVERSITE PARIS DIDEROT—PARIS 7, Paris (FR)

(72) Inventors: Nathalie Vergnolle, Toulouse (FR); Jean-Michel Sallenave, Paris (FR); Philippe Langella, Jouy en Josas (FR); Luis Bermudez-Humaran, Jouy en Josas (FR)

(73) Assignees: INSTITUT NATIONAL DE LA SANTE ET DE LA RECHERCHE MEDICALE (INSERM), Paris (FR); INSTITUT NATIONAL DE LA RECHERCHE AGRONOMIQUE (INRA), Paris (FR); UNIVERSITE PARIS DIDEROT—Paris 7, Paris (FR)

( * ) Notice: Subject to any disclaimer, the term of this patent is extended or adjusted under 35 U.S.C. 154(b) by 0 days.

(21) Appl. No.: 14/490,161

(22) Filed: Sep. 18, 2014

(65) Prior Publication Data
US 2015/0073125 A1 Mar. 12, 2015

Related U.S. Application Data

(60) Division of application No. 13/899,179, filed on May 21, 2013, now abandoned, which is a continuation of application No. 13/357,063, filed on Jan. 24, 2012, now abandoned, which is a continuation-in-part of application No. PCT/EP2011/050489, filed on Jan. 14, 2011.

(30) Foreign Application Priority Data

Jan. 14, 2010 (EP) .................................... 10305045

(51) Int. Cl.
*A01N 63/00* (2006.01)
*C07K 14/81* (2006.01)
*A61K 35/74* (2015.01)
*C12N 15/74* (2006.01)

(52) U.S. Cl.
CPC .............. *C07K 14/81* (2013.01); *A61K 35/74* (2013.01); *C07K 14/811* (2013.01); *C07K 14/8121* (2013.01); *C07K 14/8125* (2013.01); *C12N 15/746* (2013.01)

(58) Field of Classification Search
None
See application file for complete search history.

(56) References Cited

U.S. PATENT DOCUMENTS

| 5,734,014 A * | 3/1998 | Ishima et al. ................. 530/324 |
| 2004/0106564 A1 | 6/2004 | Nilius |
| 2004/0115773 A1 | 6/2004 | Arigoni et al. |
| 2005/0101005 A1* | 5/2005 | Steidler ............ C12Y 201/0104 435/252.3 |
| 2005/0276788 A1 | 12/2005 | Steidler et al. |
| 2008/0253990 A1* | 10/2008 | Steidler et al. .............. 424/85.2 |

FOREIGN PATENT DOCUMENTS

| WO | WO 96/11277 | 4/1996 |
| WO | WO 2004/001020 | 12/2003 |
| WO | WO 2005/111194 | 11/2005 |

OTHER PUBLICATIONS

Baranger et al. The Antibacterial and Antifungal Properties of Trappin-2 (pre-elafin) Do Not Depend on Its Protease Inhibitory Function. The FEBS Journal, 2008. 275:2008-2020.*
Molhuizen et al., "SKALP/elafin: an elastase inhibitor from cultured human keratinocytes," Journal of Biological Chemistry, 1993, 268: 12028-12032.*
Kato et al, Evolution of Trappin Genes in Mammals. BMC Evolutionary Biology, 2010. 10:31, pp. 1-14.*
Cotter et al (Bacteriocins: Developing Innate Immunity for Food. Nature Reviews: Microbiology, 2005. 3:777-788).*
(Continued)

*Primary Examiner* — Christopher M Babic
*Assistant Examiner* — Kimberly A Aron
(74) *Attorney, Agent, or Firm* — Vedder Price P.C.; Thomas J. Kowalski; Deborah L. Lu

(57) ABSTRACT

The present invention relates to the general field of therapy of Inflammatory Bowel Disease (IBD) and/or Irritable Bowel Syndrome (IBS). Thus, the invention relates to a molecule selected from the trappin-2 protein or an active fraction thereof, a member of the WAP family proteins or an active fraction thereof or a member of the Serpin family proteins or an active fraction thereof for the treatment of Irritable Bowel Syndrome (IBS). The invention also relates to a recombinant food-grade bacterium comprising a gene selected from a gene coding for the trappin-2 protein or an active fraction thereof, a gene coding for a member of the WAP family proteins or an active fraction thereof, or a gene coding for a member of the Serpin family proteins or an active fraction thereof.

6 Claims, 21 Drawing Sheets

(56) References Cited

OTHER PUBLICATIONS

Diep et al (Use of Lactobacilli and the Pheromone-Based Regulatory Mechanism in Gene Expression and Drug Delivery. Current Pharmaceutical Biotechnology, 2009. 10:62-73).*
Nicolas Cenac, et al., Role for Protease Activity in Visceral Pain in Irritable Bowel Syndrome, The Journal of Clinical Investigation (2007) vol. 117, No. 3, p. 636-647.
Alex C. Chin, et al., Neutrophil-Mediated Activation of Epithelial Protease-Activated Receptors-1 and -2 Regulates Barrier Function and Transepithelial Migration, J. Immunology (2008) vol. 181, No. 8, p. 5702-5710.
Eun-Young Cho, et al., Nafamostat Mesilate Attenuates Colonic Inflammation and Mast Cell Infiltration in the Experimental Colitis, International Immunopharmacology (2011) vol. 11, p. 412-417.
Isabelle Cleynen, et al., Genetic Evidence Supporting the Association of Protease and Protease Inhibitor Genes With Inflammatory Bowel Disease: A Systematic Review, PLoS One (2011) vol. 6, Issue 9, p. 1-13.
Anna G. Drannik, et al., Trappin-2/Elafin Modulate Innate Immune Responses of Human Endometrial Epithelial Cells to PolyI:C, PLos One (2012) vol. 7, Issue 4, p. 1-16.
Benoit Foligne, et al., Prevention and Treatment of Colitis With Lactococcus Lactis Secreting the Immunomodulatory Yersinia LcrV Protein, Gastroenterology (2007) vol. 133, p. 862-874.
Charles Ibeakanma, et al., Brain-Gut Interactions Increase Peripheral Nociceptive Signaling in Mice With Postinfectious Irritable Bowel Syndrome, Gastroenterology (2011) vol. 141, p. 2098-2108.
Dmitri Ivanov, et al., A Serpin From the Gut Bacterium Bifidobacterium Longum Inhibits Eukaryotic Elastase-Like Serine Proteases, The Journal of Biological Chemistry (2006) vol. 281, No. 25, p. 17246-17252.
Thierry Moreau, et al., Multifaceted Roles of Human Elafin and Secretory Leukocyte Proteinase Inhibitor (SLPI), Two Serine Protease Inhibitors of the Chelonianin Family, Biochimie (2008) vol. 90, p. 284-295.
Jean-Paul Motta, et al., Modifying the Protease, Antiprotease Pattern by Elafin Overexpression Protects Mice From Colitis, Gastroenterology (2011) vol. 140, p. 1272-1282.
Lorenzo Nissen, et al., Cloning and Detection of Serpin-Like Protein Encoding Gene in Bifidobacterium Longum Strains, Annals of Microbiology (2008) vol. 58, No. 1, p. 127-131.
Colin Reardon, et al., Thymic Stromal Lymphopoetin-Induced Expression of the Endogenous Inhibitory Enzyme SLPI Mediates Recovery From Colonic Inflammation, Immunity (2011) vol. 35, p. 223-235.
Richard Roka, et al., A Pilot Study of Fecal Serine-Protease Activity: A Pathophysiologic Factor in Diarrhea-Predominant Irritable Bowel Syndrome, Clinical Gastroenterology and Hepatology (2007) vol. 5, p. 550-555.
Jean-Michael Sallenave, et al., Elafin is Protective Against the Development of Colitis in IBD Murine Models, Gastroenterology (2008) vol. 132, No. 4, Suppl. 1, p. A-259.
R. Balfour Sartor, Therapeutic Manipulation of the Enteric Microflora in Inflammatory Bowel Diseases: Antibiotics, Probiotics and Prebiotics, Gastroenterology (2004) vol. 126, p. 1620-1633.
Lothar Steidler, et al., Treatment of Murine Colitis by Lactococcus Lactis Secreting Interleukin-10, Science (2000) vol. 259, p. 1352-1355.
Lothar Steidler, et al., Biological Containment of Genetically Modified Lactococcus Lactis for Intestinal Delivery of Human Interleukin 10, Nature Biotechnology (2003) vol. 21, No. 7, p. 785-789.
Lothar Steidler, et al., Therapeutic Drug Delivery by Genetically Modified Lactococcus Lactis, Annals New York Academy of Sciences (2006) vol. 1072, p. 176-186.
Maria C. Urdaci, et al., Some Immunomodulatory Effects of Probiotic Bacteria Might Be Due to Porcine Neutrophil Elastase Inhibitor, A Serpin Present in MRS Broth, Immunology Letters (2009) vol. 122, p. 99-100.

* cited by examiner

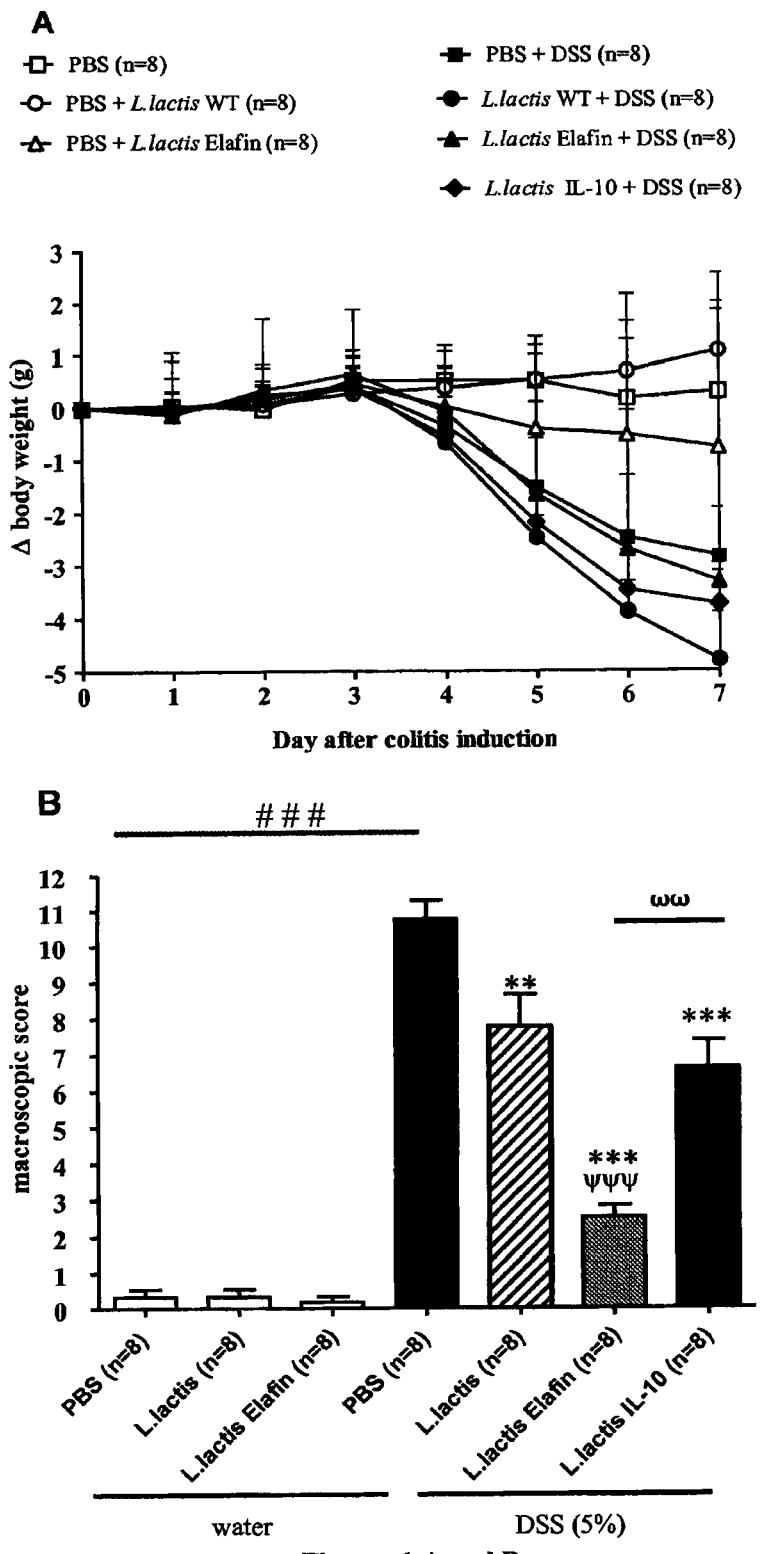
Figures 1 A and B

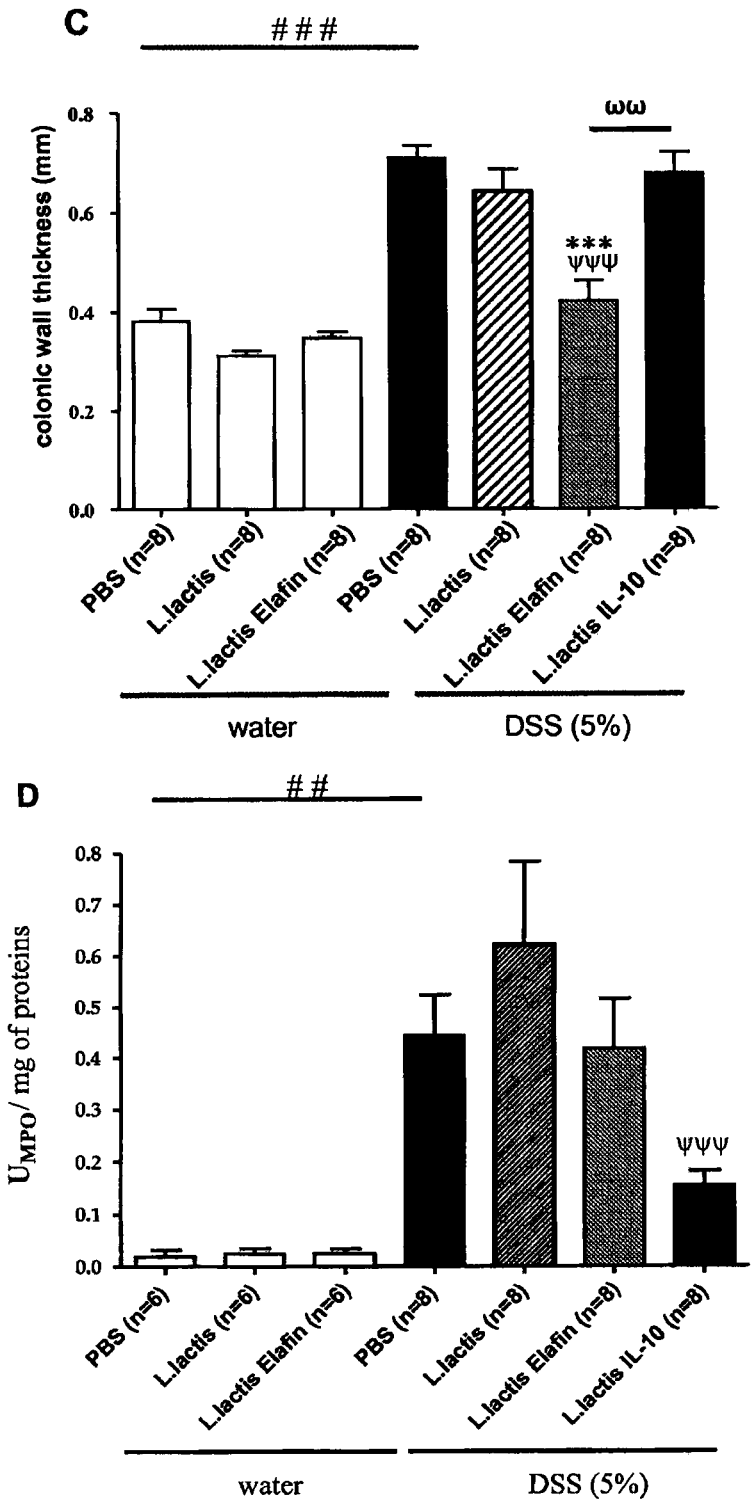
Figures 1 C and D

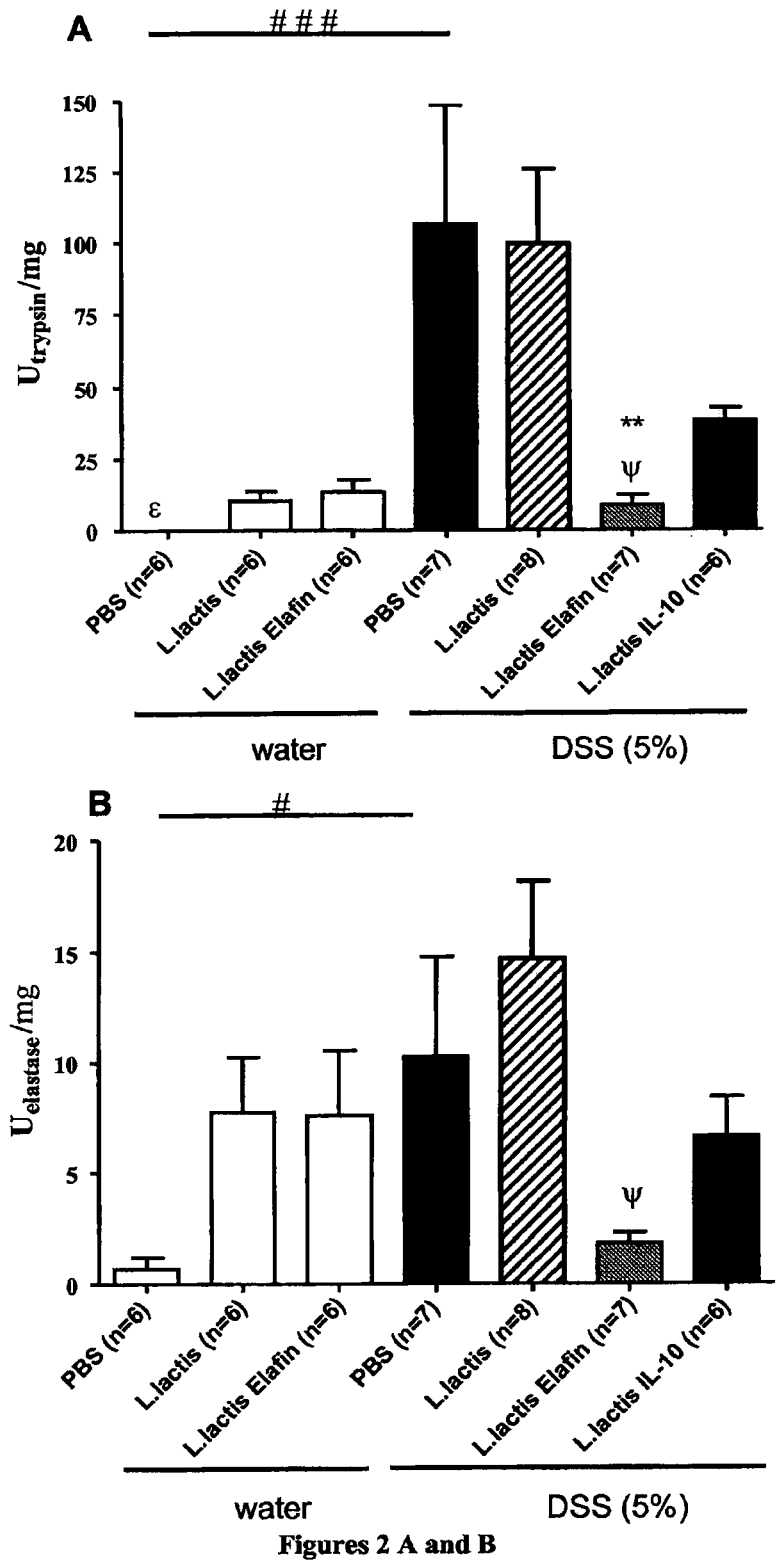
Figures 2 A and B

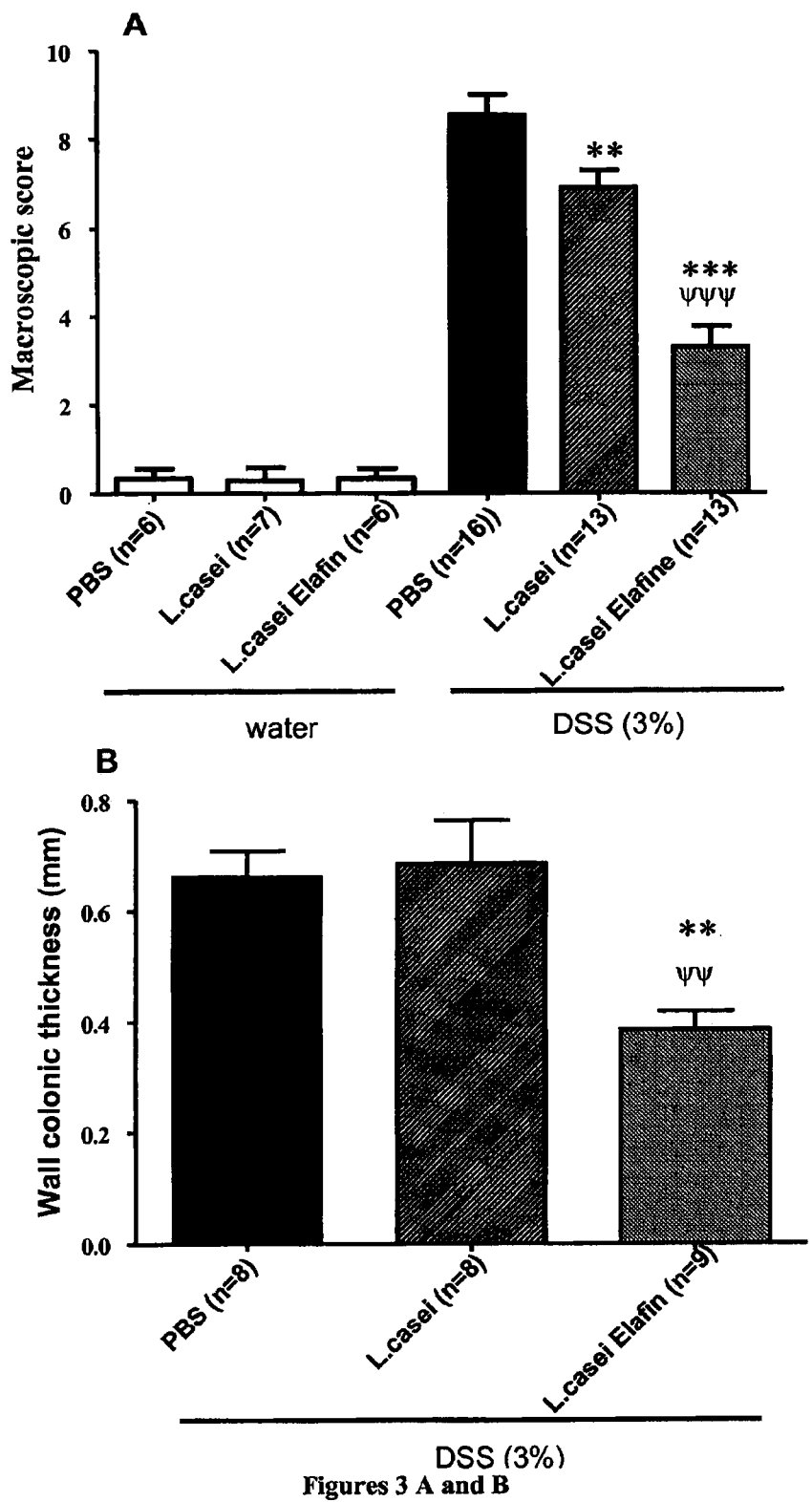
Figures 3 A and B

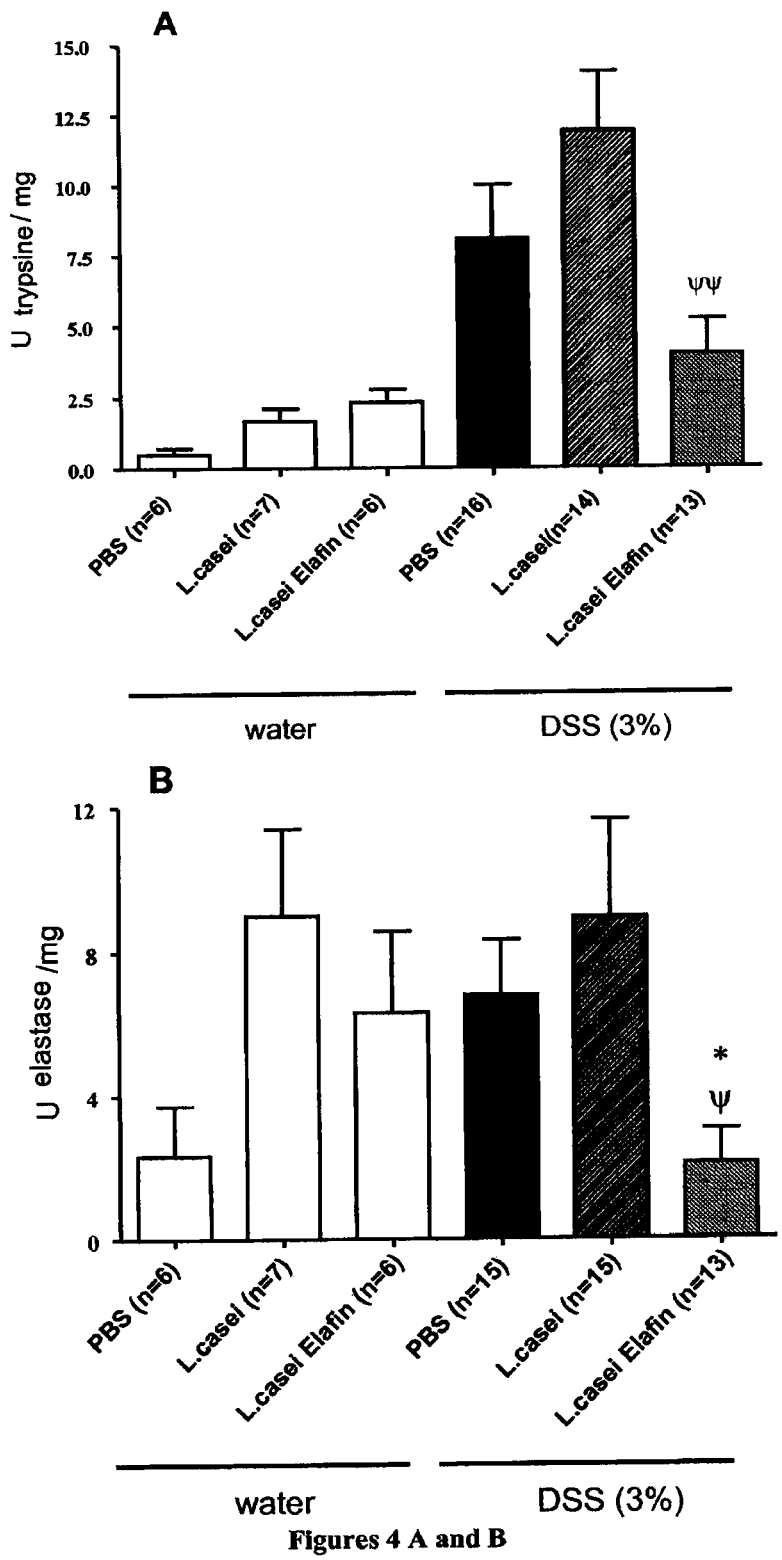
Figures 4 A and B

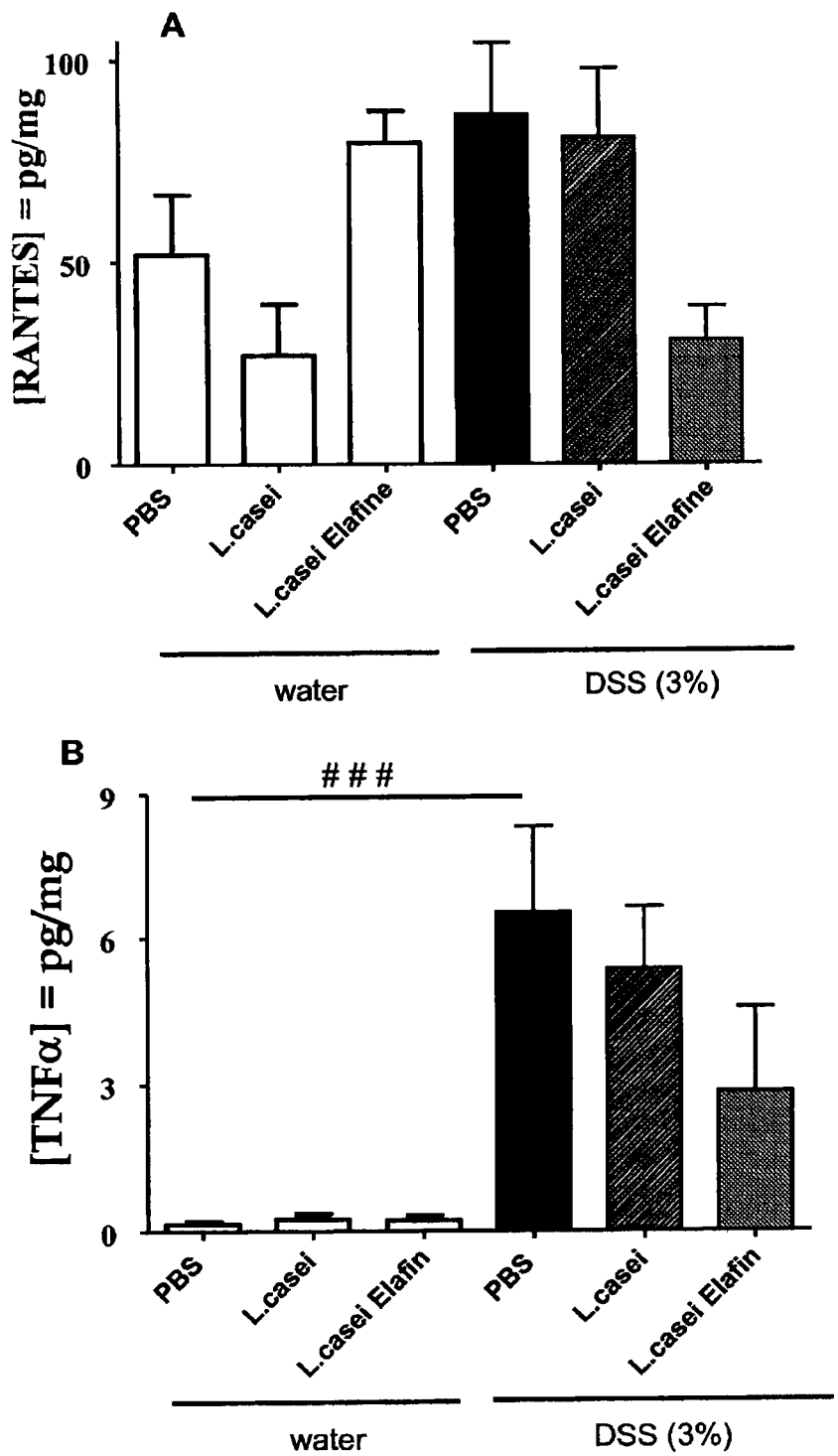
Figures 5 A and B

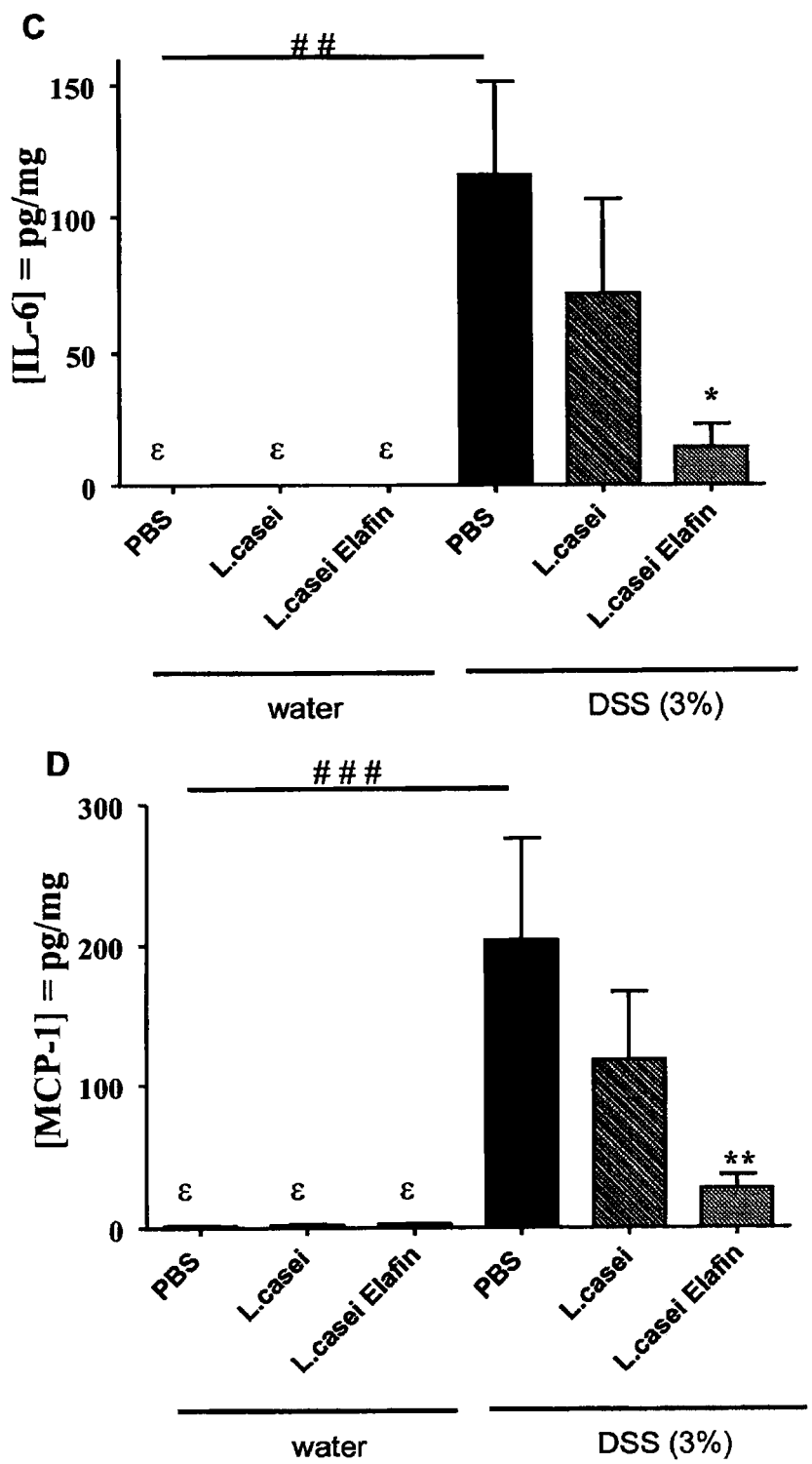
Figures 5 C and D

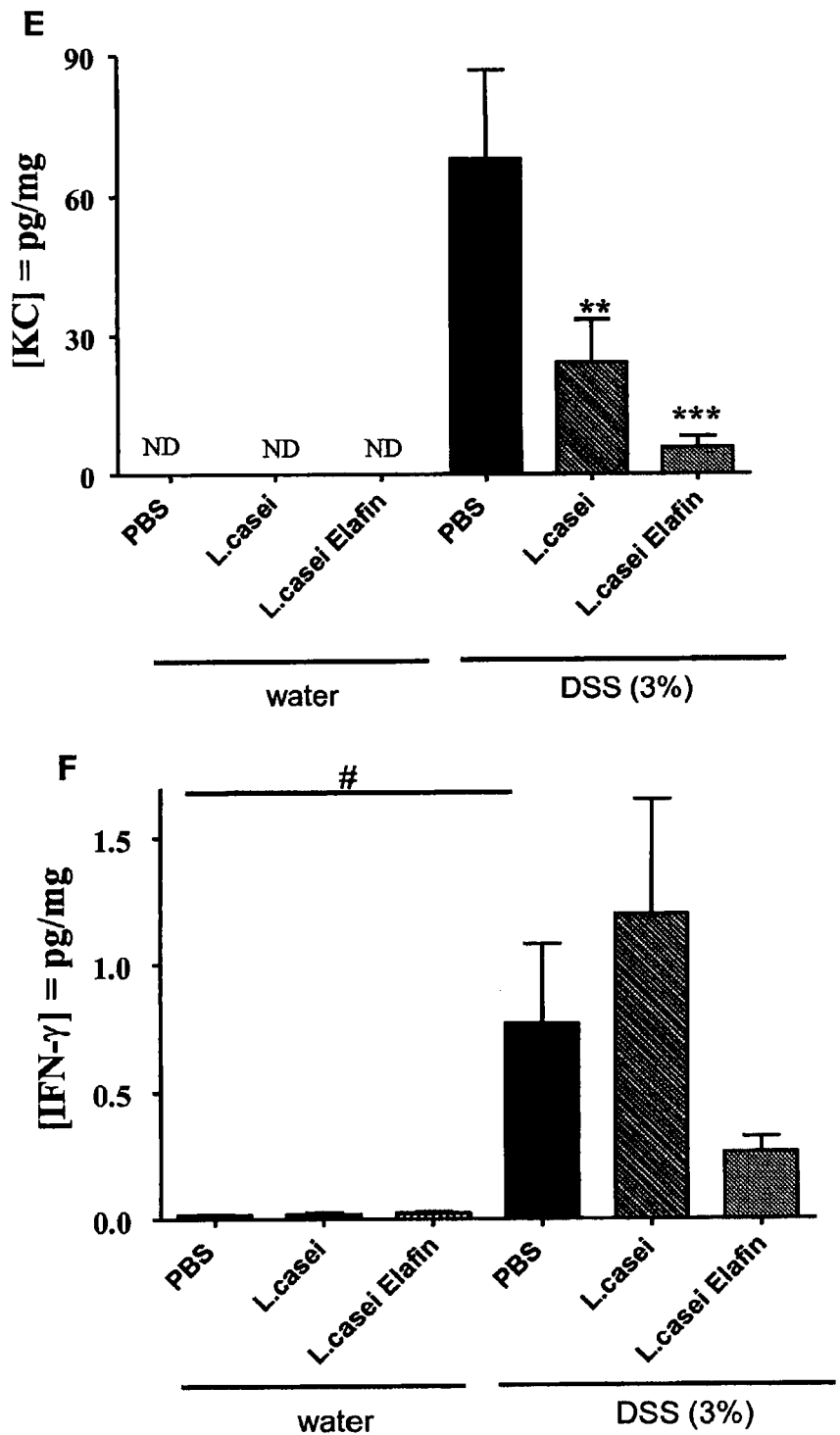
Figures 5 E and F

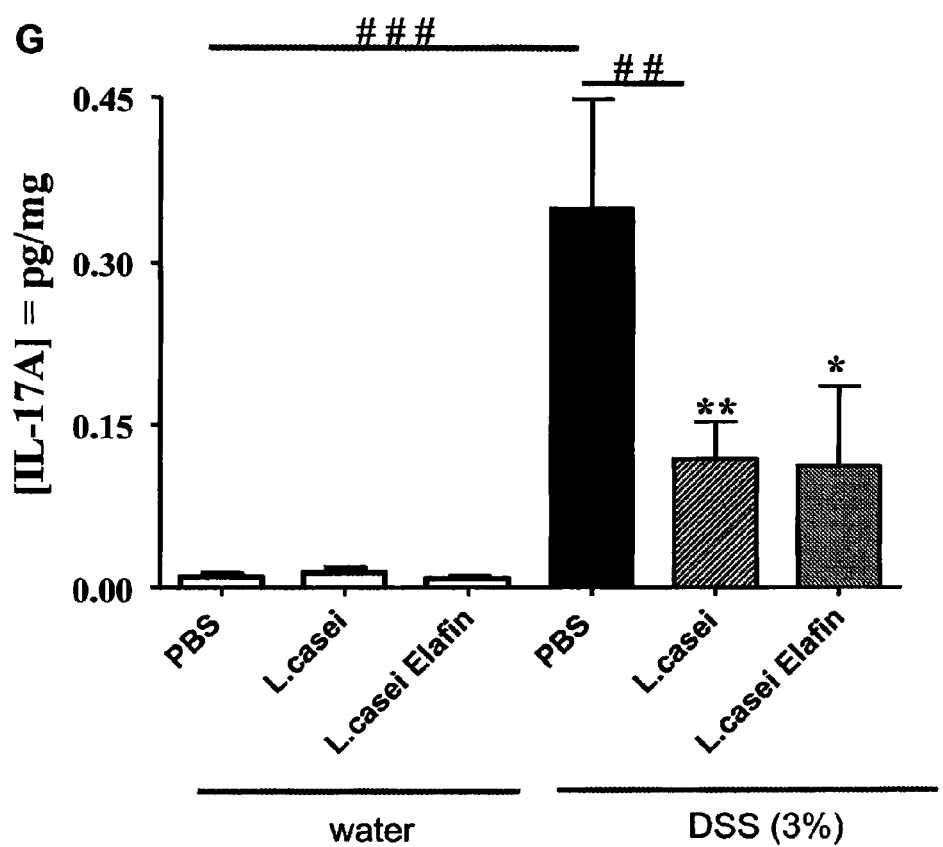

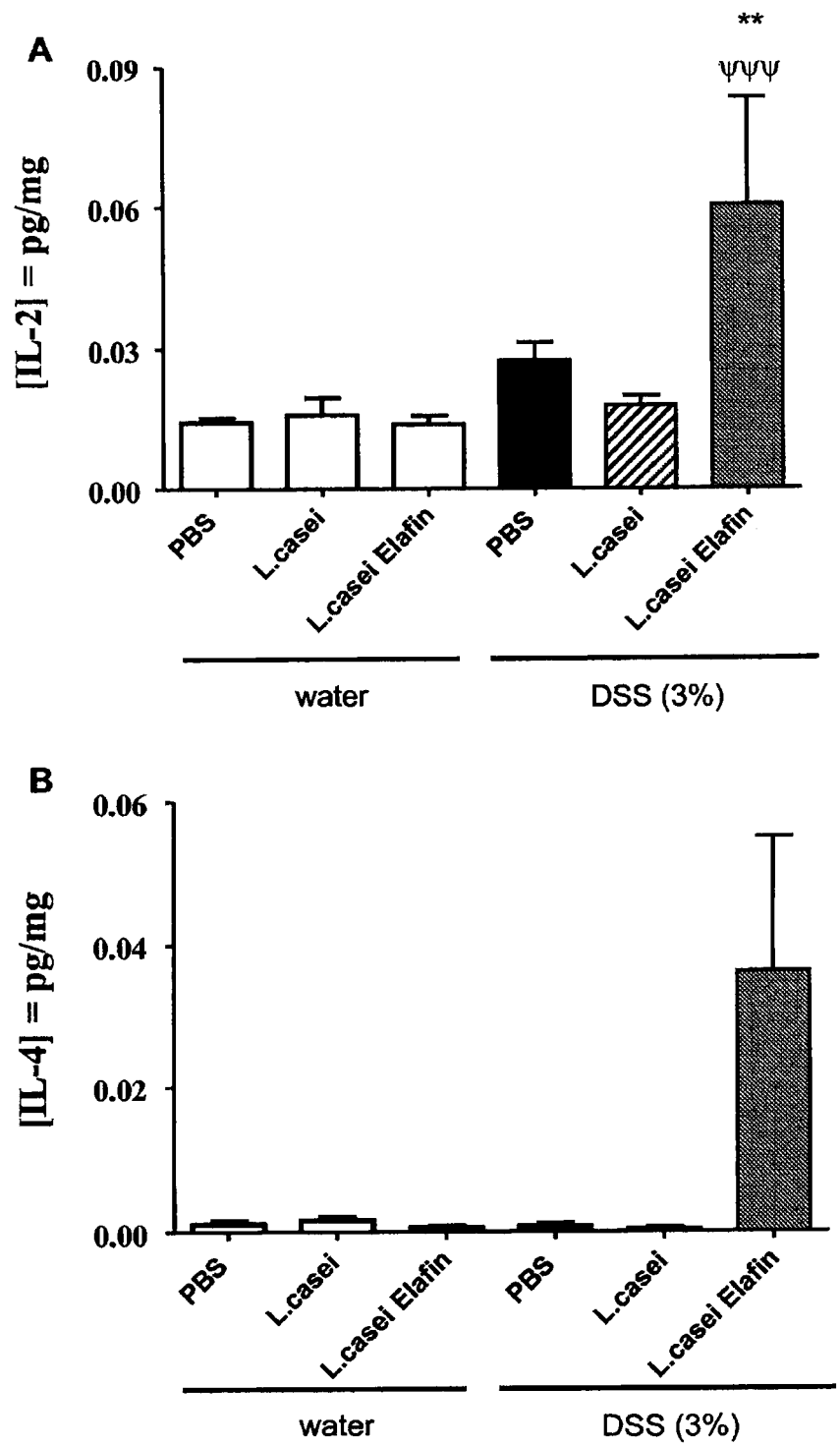
Figures 6 A and B

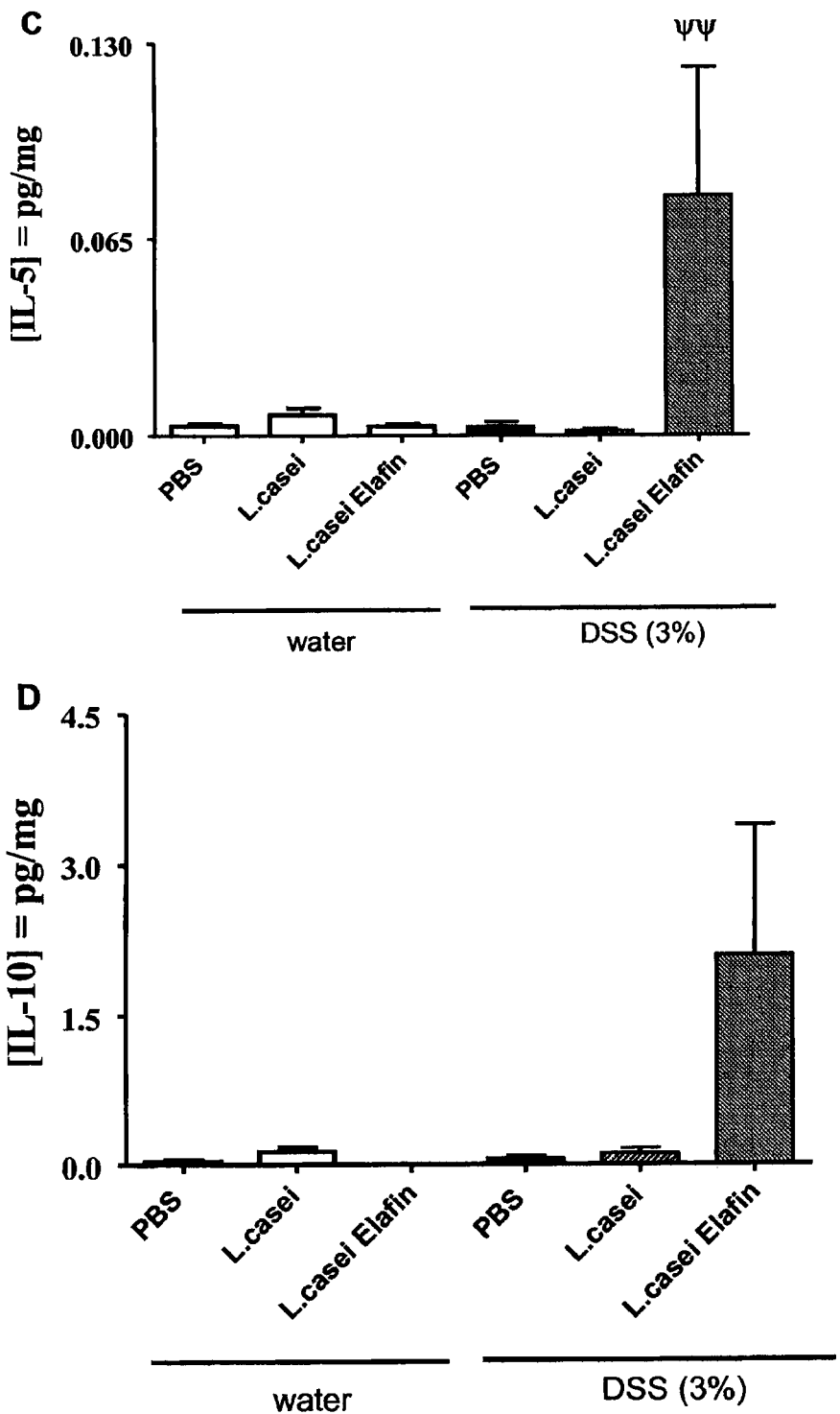
Figures 6 C and D

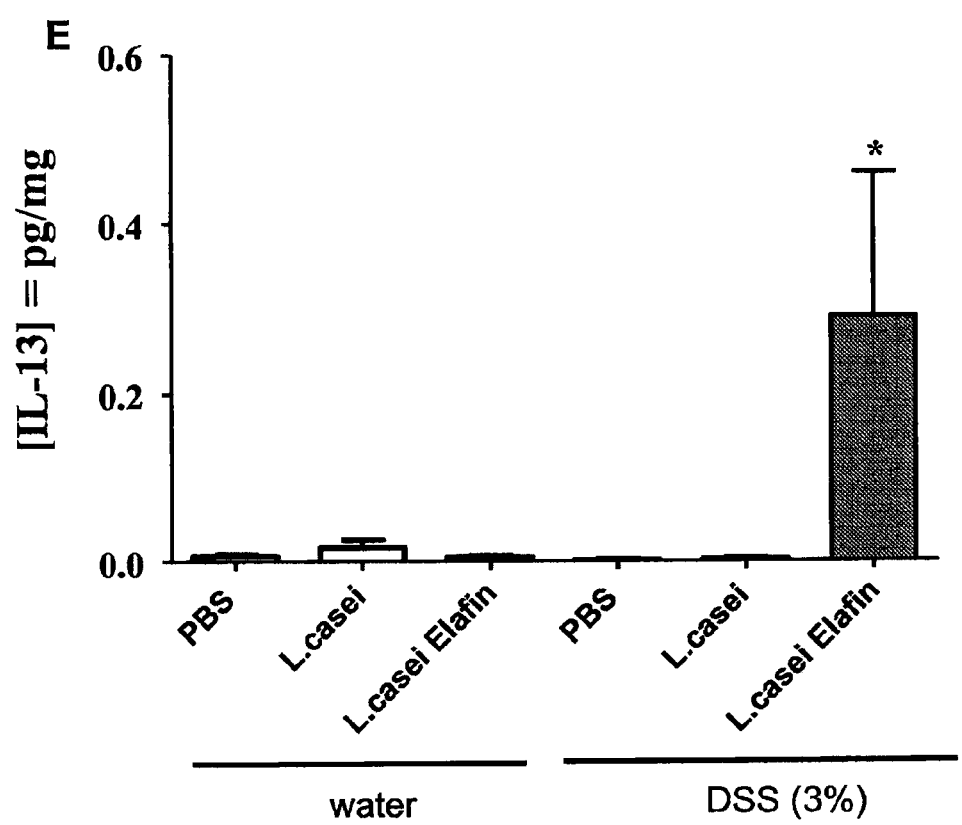

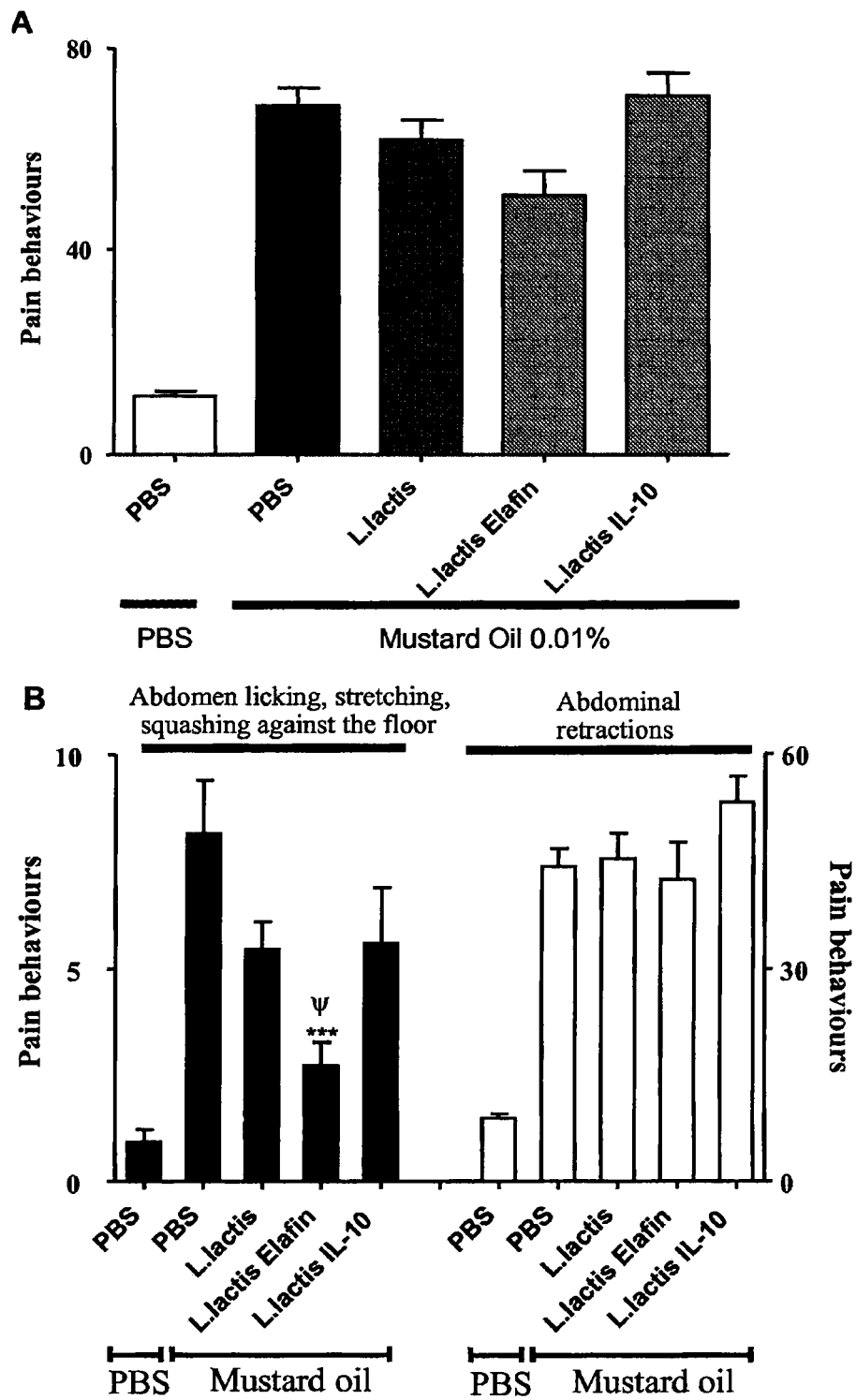
Figures 7 A and B

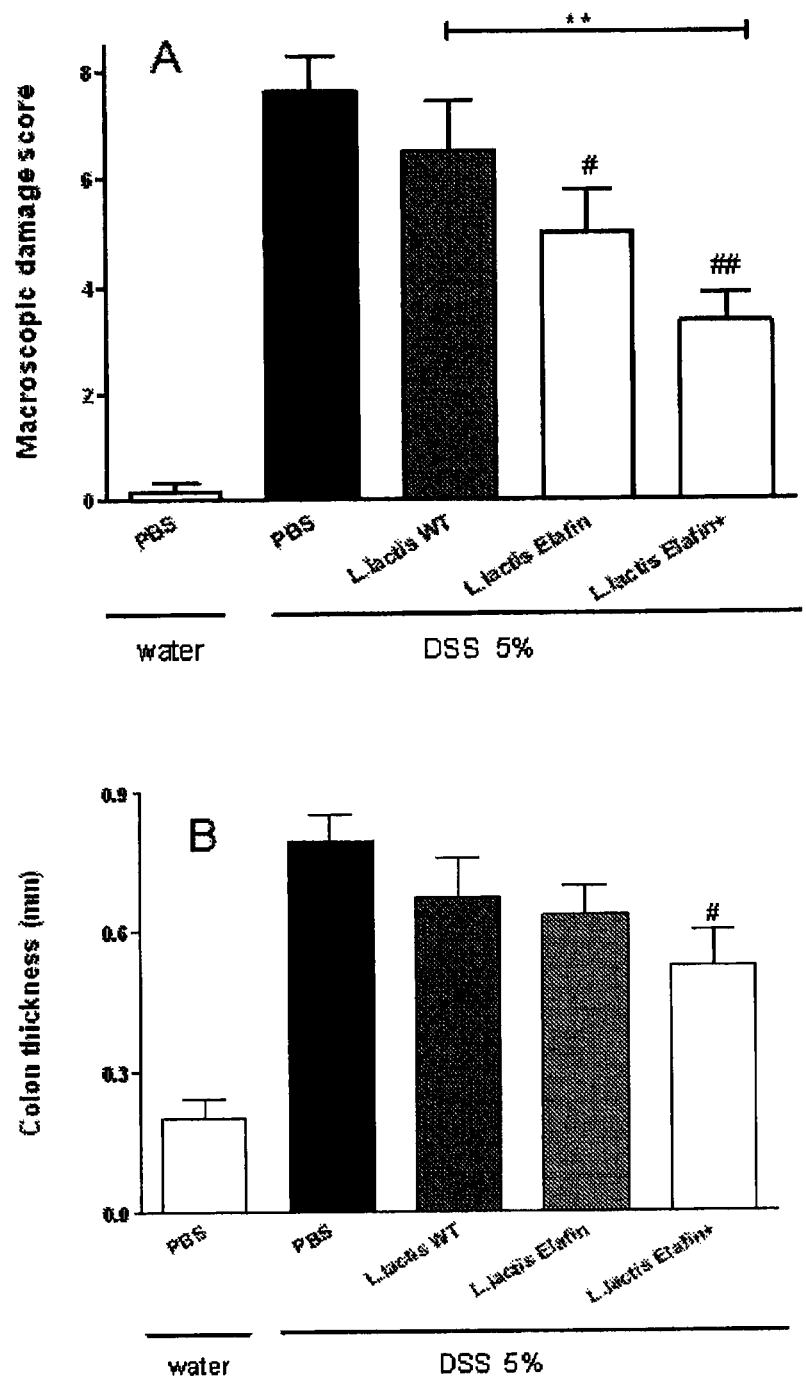
Figure 9 A and B

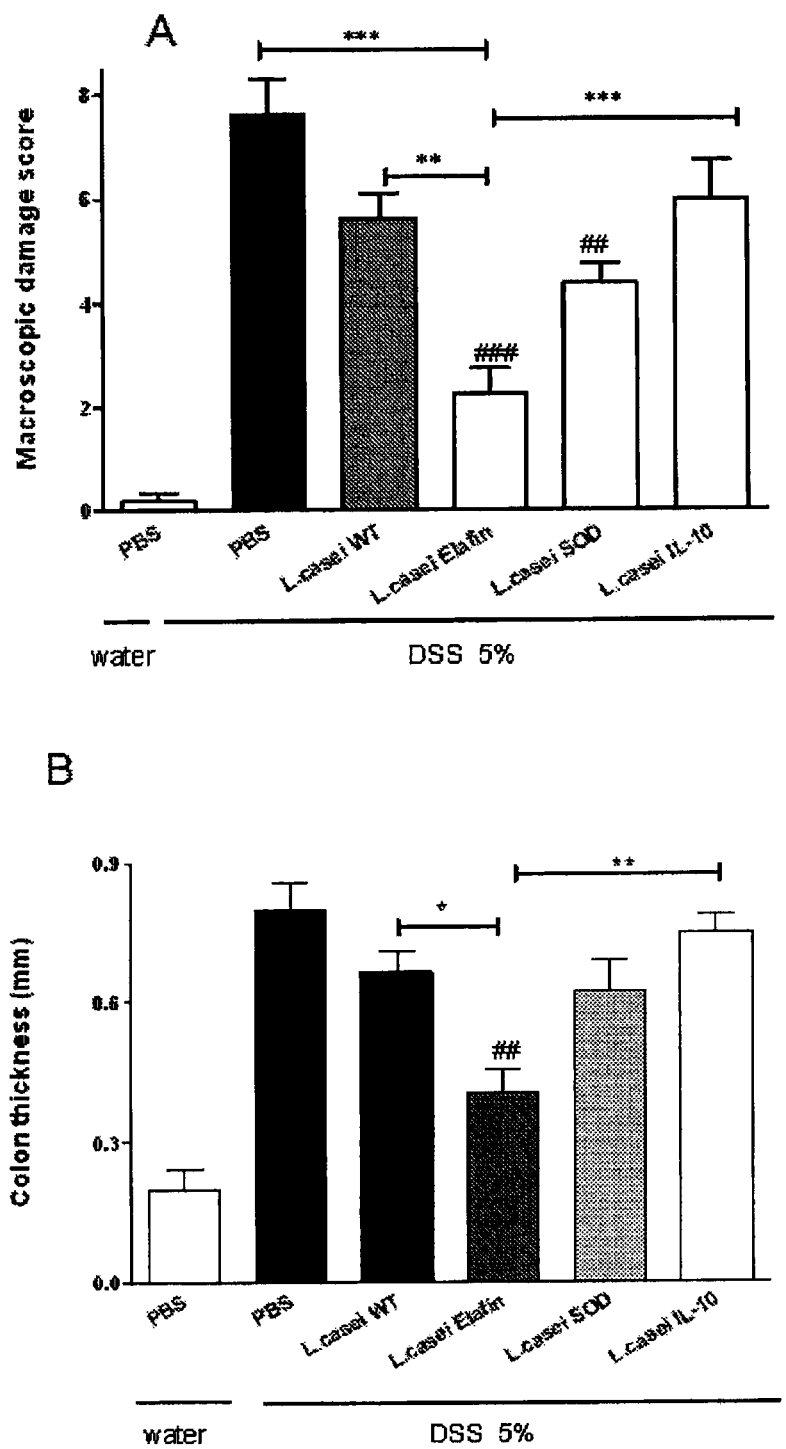
Figures 10 A and B

RECOMBINANT PROBIOTIC BACTERIA FOR THE PREVENTION AND TREATMENT OF INFLAMMATORY BOWEL DISEASE (IBD) AND IRRITABLE BOWEL SYNDROME (IBS)

RELATED APPLICATIONS AND INCORPORATION BY REFERENCE

This application is a divisional application of now abandoned patent application Ser. No. 13/899,179 filed 21 May 2013 which is a continuation of now abandoned patent application Ser. No. 13/357,063 filed 24 Jan. 2012 which is a continuation-in-part application of international patent application Serial No. PCT/EP2011/050489 filed 14 Jan. 2011, which published as PCT Publication No. WO 2011/086172 on 21 Jul. 2011, which claims benefit of European patent application Serial No. 10305045.6 filed 14 Jan. 2010.

The foregoing applications, and all documents cited therein or during their prosecution ("appln cited documents") and all documents cited or referenced in the appln cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention. More specifically, all referenced documents are incorporated by reference to the same extent as if each individual document was specifically and individually indicated to be incorporated by reference.

SEQUENCE LISTING

The instant application contains a Sequence Listing which has been submitted electronically in ASCII format and is hereby incorporated by reference in its entirety. Said ASCII copy, created on Nov. 13, 2014, is named 44241.02.2001_SL.txt and is 1,324 bytes in size.

FIELD OF THE INVENTION

The present invention relates to the general field of therapy of gut inflammatory diseases such as Inflammatory Bowel Diseases (IBD), pulmonary diseases such as cystic fibrosis and broncho-pulmonary chronic obstructive diseases (BPCO), inflammatory articular disease (such as osteoarthritis), inflammatory urogenital disease, and diseases associated with chronic visceral pain symptoms, such as Irritable Bowel Syndrome (IBS).

BACKGROUND OF THE INVENTION

The treatment of chronic inflammatory disorders such as IBD represents a major medical challenge as they afflict several millions of persons. Its highest incidence is among developed countries and has been increasing steadily over the past 3 decades. Current therapies for IBD strongly need to be improved, a high percentage of patients (between 20 and 40%) being resistant to any forms of treatments, severe side effects and high costs being also associated to the currently available drugs (glucocorticoids and monoclonal antibody therapies). In addition, the mechanisms involved in the pathogenesis of IBD are not fully understood, and the development of more effective treatments or even cures for IBD depends upon better understanding the regulation of the inflammatory response. Several studies have demonstrated a crucial role for proteases in the maintenance of chronic inflammatory response of the gastrointestinal tract (GIT) [Vergnolle, N. 2005; Cenac, N. et al., 2007; Hyun, E., et al., 2008; Vergnolle, N., et al., 2004]. Therefore, endogenous protease inhibitors seem to be crucial to the control of intestinal inflammatory responses.

Based on this knowledge, the inventors propose that delivery of those protease inhibitors into the GIT, could be used for the treatment of an IBD and/or irritable Bowel syndrome (IBS).

The use of probiotics for the treatment of IBD has now been proposed for several years and different studies have reported some beneficial effects of these probiotic bacteria tested alone or in combination [Hedin, C. et al., 2007; Sartor, R. B. 2004]. The strategy of using recombinant non-pathogenic food-grade bacteria as delivery vehicles of anti-inflammatory molecules at the mucosal level has already been used to deliver the anti-inflammatory cytokine IL-10 [Steidler, L., et al., 2000]. Phase I clinical trials have demonstrated that orally given *Lactococcus lactis* strain expressing IL-10 cytokine, was safe as no serious side-effects occurred in those patients [Braat, H., et al., 2006]. However, the decreased disease activity in Crohn's disease patients treated with IL-10 recombinant *L. lactis* was somehow limited. This limited efficacy could be explained by the fact that IL-10 delivery has always been reported to have only discrete beneficial effects against the development of colitis [Braat, H. et al., 2003].

Citation or identification of any document in this application is not an admission that such document is available as prior art to the present invention.

SUMMARY OF THE INVENTION

The invention is based on the discovery that the use of a food-grade bacterium to deliver an anti-inflammatory molecule such as trappin-2 provides a safety and better efficiency than existing treatments. A better choice in the nature of the anti-inflammatory molecule to be delivered by *L. lactis*, could thus considerably improve the efficacy of treatment. Here, the inventors propose to use a food-grade bacterium to express and deliver anti-protease trappin-2 into the gut.

Thus, the invention relates to a molecule selected from the trappin-2 protein or an active fraction of the trappin-2 protein, a member of the WAP family proteins or an active fraction of a member of the WAP family proteins or a member of the Serpin family proteins or an active fraction of a member of the Serpin family proteins for the treatment of Irritable Bowel Syndrome (IBS).

A further object of the invention relates to a recombinant food-grade bacterium comprising a gene selected from a gene coding for the trappin-2 protein or an active fraction of the trappin-2 protein, a gene coding for a member of the WAP family proteins or an active fraction of a member of the WAP family proteins, or a gene coding for a member of the Serpin family proteins or an active fraction of a member of the Serpin family proteins.

Another aspect of the invention relates to a therapeutic composition comprising a recombinant food-grade bacterium as defined above.

Accordingly, it is an object of the invention to not encompass within the invention any previously known product, process of making the product, or method of using the product such that Applicants reserve the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (35 U.S.C. §112, first paragraph) or the EPO (Article 83 of the EPC), such that Applicants reserve the right and hereby disclose a disclaimer of any previously described product, process of making the product, or method of using the product.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

These and other embodiments are disclosed or are obvious from and encompassed by, the following Detailed Description.

BRIEF DESCRIPTION OF THE DRAWINGS

The following detailed description, given by way of example, but not intended to limit the invention solely to the specific embodiments described, may best be understood in conjunction with the accompanying drawings.

FIGS. 1A-D: Weight differences (A), macroscopic score (B), Wall thickness (C), and myeloperoxydase (MPO) activity (D) in colonic tissues from mice that had water or water+DSS (3%) in their dinking bottles, and that received daily oral treatments for 7-days with wild-type *L. lactis*, or recombinant *L. lactis* strains expressing either Elafin or IL-10. Significant differences compared to PBS-treated mice that have received DSS were noted * for p<0.05,  for p<0.01, and * for p<0.005. Significant differences compared to wild-type *L. lactis*-treated mice were noted Ψ for p<0.05, ΨΨ for p<0.01, and ΨΨΨ for p<0.05. Significant differences between PBS+DSS group and the PBS-water group were noted # for p<0.05, ## for p<0.01, and ### for p<0.005. Significant differences compared to the IL-10 recombinant *L. lactis* group were noted ω for p<0.05, ωω for p<0.01, and ωωω for p<0.005.

FIGS. 2A-B: Trypsin-like activity (A) and elastase activity (B) in washes of the colonic lumen of mice that had water or water+DSS (3%) in their drinking bottles, and that received daily oral treatments for 7-days with wild-type *L. lactis*, or recombinant *L. lactis* strains expressing either Elafin or IL-10. ε means undetectable levels. Significant differences compared to PBS-treated mice that have received DSS were noted * for p<0.05, ** for p<0.01. Significant differences compared to wild-type *L. lactis*-treated mice were noted Ψ for p<0.05. Significant differences between PBS+DSS group and the PBS-water group were noted # for p<0.05, ## for p<0.01, and ### for p<0.005.

FIGS. 4A-B: Trypsin-like activity (A) and elastase activity (B) in washes of the colonic lumen of mice that had water or water+DSS (3%) in their dinking bottles, and that received daily oral treatments for 7-days with wild-type *Lb. casei*, or recombinant *Lb. casei* expressing elafin. Significant differences compared to PBS-treated mice that have received DSS were noted * for p<0.05, and significant differences compared to wild-type *Lb. casei*-treated mice were noted Ψ for p<0.05, and ΨΨ for p<0.01.

FIGS. 5A-G: Protein concentration of RANTES (A), TNFα (B), IL-6 (C), MCP-1 (D), KC (E), INFγ (F) and IL-17 (G) detected in colonic tissues from mice that had water or water+DSS (3%) in their dinking bottles, and that received daily oral treatments for 7-days with wild-type *Lb. casei*, or recombinant *Lb. casei* expressing Elafin. ε means undetectable levels. Significant differences compared to PBS-treated mice that have received DSS were noted * for p<0.05,  for p<0.01, and * for p<0.005. Ψ showed significant differences for p<0.05, compared to mice treated with wild-type *L. lactis*. Significant differences between PBS+DSS group and the PBS-water group were noted # for p<0.05, ## for p<0.01, and ### for p<0.005.

FIGS. 6A-E: Protein concentration of IL-2 (A), IL-4 (B), IL-5 (C), IL-10 (D) and IL-13 (E) detected in colonic tissues from mice that had water or water+DSS (3%) in their dinking bottles, and that received daily oral treatments for 7-days with wild-type *Lb. casei*, or recombinant *Lb. casei* expressing Elafin. Significant differences compared to PBS-treated mice that have received DSS were noted * for p<0.05, and ** for p<0.01. Significant differences compared to mice treated with wild-type *Lb. casei* were noted Ψ for p<0.05, and ΨΨ for p<0.01.

FIGS. 7A-B: Total number of pain behaviors (A) or number of abdominal contractions and licking, stretching and squashing behaviors (B) in mice that have received intracolonically PBS (n=5), or Mustard oil (0.01% (v/v) in ethanol 70%), and that have received in for the previous 7-days, pre-treatments by oral gavage of PBS (n=8), wild-type *L. lactis* (n=8), or recombinant *L. lactis* expressing either elafin (n=8) or IL-10 (n=5). Significant differences compared to PBS-treated mice that have received mustard oil were noted * for p<0.05,  for p<0.01, and * for p<0.005. Ψ showed significant differences for p<0.05, compared to mice treated with wild-type *L. lactis*.

FIGS. 10A-C: Protective effects of *L. casei* wt strain and SOD-expressing, elafin-expressing and IL-10-expressing *L.* casei strains in DSS 5%-induced colitis model. Macroscopic (A), histological damages (B) and MPO activities (C) were evaluated in different groups of 10 mice treated either with water (negative control) or with DSS 5%. Two first control groups were treated i) with water and orally fed with PBS (negative control group) and ii) with DSS 5% and orally fed with PBS (positive control group). The other groups were all treated with DSS 5% and with either *L. casei* wt strain (WT) or *L. casei* strains expressing superoxide dismutase (SOD), elafin (Elafin) or IL-10. * and ** indicate that the data are significantly different (P<0.05) from the data obtained with *L. casei* wt.

Figure 11:
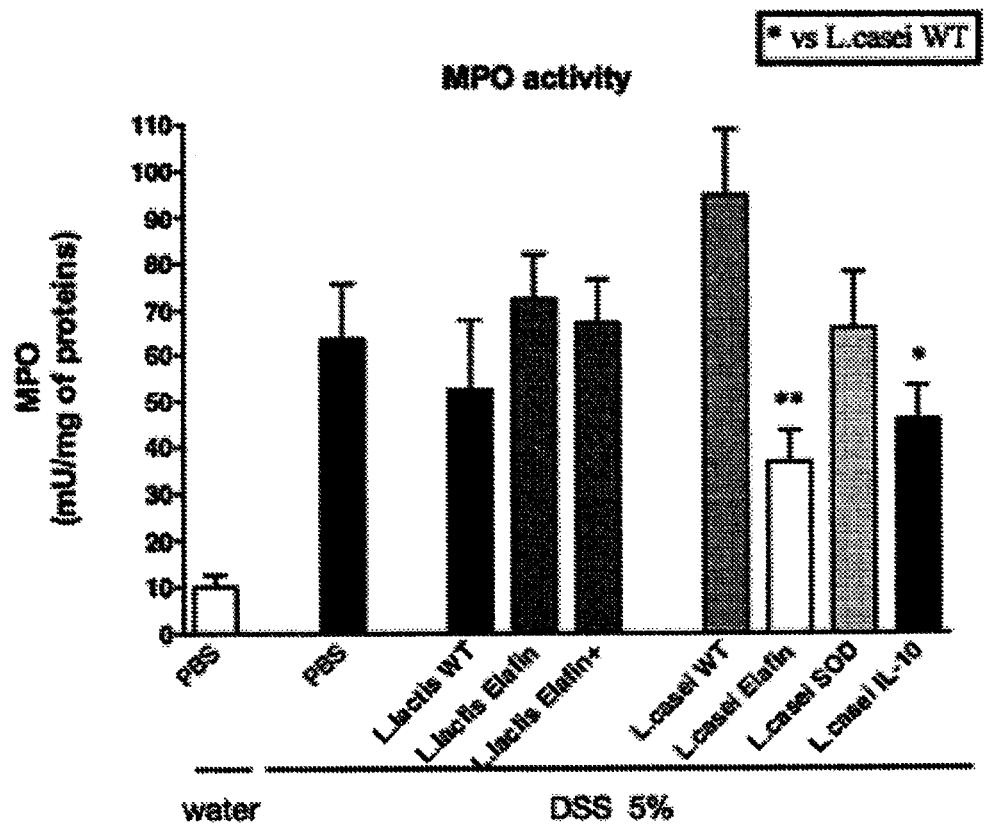

FIG. 11: Myeloperoxydase (MPO) activity (D) in colonic tissues from mice. Myeloperoxydase (MPO) activity (D) was measured in colonic tissues from mice that had water or water+DSS (3%) in their clinking bottles, and that received daily oral treatments for 7-days with i) WT *L. lactis*, recombinant *L. lactis* and *L. lactis* htrA strains expressing either Elafin or IL-10 and with ii) *L. casei* wt strain and SOD-expressing, elafin-expressing and IL-10-expressing *L. casei* strains. * and ** indicate that the data are significantly different (P<0.05) from the data obtained with *L. casei* wt.

Figure 12:
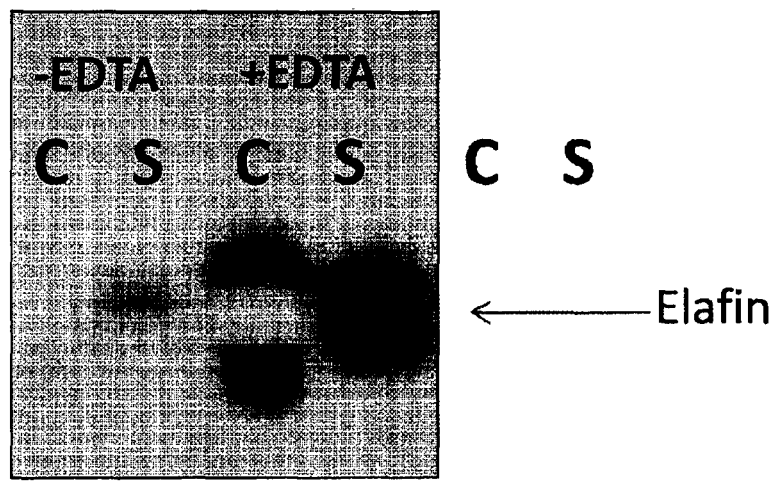

FIG. 12: Elafin secretion in a *L. lactis* WT strain where the elafin gene is expressed under the control of an EDTA-inducible promoter [Llull D and Poquet I. 2004; EP 1 537 215 and FR 98 16462]. The *L. lactis* WT strain expressing elafin was grown overnight in the presence (+) or not (−) of EDTA, a chelator agent (in this construct, elafin gene expression is controlled by a lactococcal promoter that may be induced by EDTA addition: on the chromosome, this promoter controls the expression of genes encoding an ABC uptake system specific for zinc and is derepressed under zinc starvation conditions that may be mimicked by EDTA addition). Proteins were then extracted and fractionated between cell (C) and supernatant fractions (S) and Western blot experiments were performed using antibodies anti-elafin.

DETAILED DESCRIPTION OF THE INVENTION

As used herein, the term "trappin-2" (also known as elafin, elafin-specific inhibitor (ESI) or SKALP for skin anti-leucoprotease) of the WAP family, denotes a low molecular weight (9.9 kDa) inhibitor of HNE (human neutrophil elastase) and proteinase 3, which is secreted in the respiratory tract [Sallenave et al., 1991 and 1993]. Along with (A1-Pi) and SLPI, trappin-2 comprises an integral part of the 'anti-elastase shield' in the lung. An exemplary sequence for human trappin-2 gene is deposited in the database Genbank under accession number S58717.

As used herein, the term "WAP family" for "Whey Acidic Protein" denotes a family of protein containing the trappin-2, and the ps20.

As used herein, the term "Serpin family" for SERine Protease INhibitors denotes a family of serine proteinase inhibitors which are similar in amino acid sequence and mechanism of inhibition, but differ in their specificity toward proteolytic enzymes. This family includes alpha 1-antitrypsin (A1-Pi), angiotensinogen, ovalbumin, antiplasmin, alpha 1-antichymotrypsin, thyroxine-binding protein, complement 1 inactivators, antithrombin III, heparin cofactor II, plasminogen inactivators, gene Y protein, placental plasminogen activator inhibitor, and barley Z protein. This family does not include the secretory leukocyte proteinase inhibitor (SLPI) [Thierry Moreau et al., 2008]. Some members of the Serpin family may be substrates rather than inhibitors of serine endopeptidases, and some serpins occur in plants where their function is not known.

As used herein, the term "alpha 1-antitrypsin protein" denotes a glycoprotein. Alpha 1-antitrypsin is also referred to as alpha-1 proteinase inhibitor (A1PI) because it is a serine protease inhibitor (serpin), inhibiting a wide variety of proteases. It protects tissues from enzymes of inflammatory cells, especially elastase. An exemplary sequence for human Alpha 1-antitrypsin gene is deposited in the database Genbank under accession number NC008290.

As used herein, the term "an active fraction of denotes a fraction of a protein with the activity of the complete protein". For example, an active fraction of the trappin-2 protein denotes a fraction of the protein which conserves the capacity to inhibit the FINE or an active fraction of the Serpin family proteins denotes a fraction of the protein which conserves the capacity of inhibition.

As used herein, the term "food-grade bacterium" denotes a bacterium that is widely used in fermented foods and possesses a perfect safety profile recognized by the GRAS (Generally Recognized As Safe) and QPS (Qualified Presumption of Safety) status in USA and European Community, respectively. Such bacterium may be safely in functional foods or food additives with allegations concerning maintain in good health and well-being or prevention of disease.

As used herein, the term "probiotic bacterium" denotes a bacterium which ingested live in adequate quantities may exert beneficial effects on the human health. They are now widely used as a food additive for their health-promoting effects. Most of the probiotic bacteria are Lactic Acid Bacterium (LAB) and among them strains of the genera *Lactobacillus* and *Bifidobacterium* are the most widely used probiotic bacteria.

As used herein, the term "thyA gene" denotes, the gene coding for thymidylate synthase which is an enzyme generating thymidine monophosphate (dTMP), which is subsequently phosphorylated to thymidine triphosphate used in DNA synthesis and repair.

As used herein, the term "Irritable Bowel Syndrome (IBS)" is a term for a variety of pathological conditions causing discomfort in the gastro-intestinal tract. It is a functional bowel disorder characterized by chronic abdominal pain, discomfort, bloating, and alteration of bowel habits in the absence of any organic cause.

As used herein, the term "inflammatory bowel diseases (IBD)" is a group of inflammatory diseases of the colon and small intestine. The major types of IBD are Crohn's disease, ulcerative colitis and pouchitis.

A first object of the invention relates to a molecule selected from the trappin-2 protein or an active fraction of the trappin-2 protein, a member of the WAP family proteins or an active fraction of a member of the WAP family proteins, or a molecule selected from the Serpin family or an active fraction of the Serpin family for the treatment of Irritable Bowel Syndrome (IBS).

In a preferred embodiment, the member of the Serpin family may be the alpha 1-antitrypsin protein.

In a preferred embodiment, said fraction of the protein comprises at least about 75% identity over said protein, even more preferably at least about 80%, at least about 85%, at least about 90%, at least about 95%, at least about 97%, at least about 99%.

Typically said protein or fraction of the protein thereof may be used in combination with an anti-inflammatory agent.

Proteins of the invention or fractions of the proteins thereof may be produced by any technique known per se in the art, such as, without limitation, any chemical, biological, genetic or enzymatic technique, either alone or in combination(s).

Knowing the amino acid sequence of the desired sequence, one skilled in the art may readily produce a relevant part of the said proteins or fraction of the protein, by standard techniques for production of proteins. For instance, they may be synthesized using well-known solid phase method, preferably using a commercially available protein synthesis apparatus (such as that made by Applied Biosystems, Foster City, Calif.) and following the manufacturer's instructions.

Alternatively, the proteins or fraction of the proteins of the invention thereof may be synthesized by recombinant DNA techniques as is now well-known in the art. For example, these fragments may be obtained as DNA expression products after incorporation of DNA sequences encoding the desired polypeptide into expression vectors and introduction of such vectors into suitable eukaryotic or prokaryotic hosts that will express the desired protein or fraction of the protein, from which they may be later using well-known techniques.

Proteins or fraction of the proteins of the invention thereof may be used in an (e.g., purified) form or contained in a vector, such as a membrane or lipid vesicle (e.g. a liposome).

A further object of the invention relates to a recombinant food-grade bacterium comprising a gene selected from a gene coding for the trappin-2 protein or an active fraction of the trappin-2 protein, a gene coding for a member of the WAP family proteins or an active fraction of a member of the WAP family proteins, or a gene coding for a member of the Serpin family proteins or an active fraction of a member of the Serpin family proteins.

In a preferred embodiment, the food-grade bacterium according to the invention may be a probiotic bacterium.

In a preferred embodiment, the probiotic bacterium according to the invention comprises a defective auxotrophic gene, whereby survival of said bacterium may be strictly dependent upon the presence of specific compounds.

In another preferred embodiment, the auxotrophic gene according to the invention may be the thyA gene encoding the thymidylate synthase.

In another preferred embodiment, the auxotrophic gene according to the invention may be the alanine racemase (alr) gene [Bron et al, 2002].

Inactivation of the thyA gene of the probiotic bacterium according to the invention renders it auxotrophic to thymidine which is absent from the gastrointestinal tract (GIT). This recombinant thyA mutant will be able to deliver its protein of interest but will not survive and thus persist in GIT limiting its dissemination and conferring the requested biological containment for recombinant bacteria. Similar results may be obtained with alr gene.

In another preferred embodiment, the selected gene may be inserted in the thyA gene.

Preferably, the recombinant gene may be located in the chromosome into the thyA gene locus which may be thus inactivated by gene disruption. As used herein, the term "gene disruption" denotes disruption by insertion of a DNA fragment, disruption by deletion of the gene, or a part thereof, as well as exchange of the gene or a part thereof by another DNA fragment, and the disruption may be induced by recombinant DNA techniques, and not by spontaneous mutation. Preferably, disruption is the exchange of the gene, or a part thereof, by another functional gene. Preferably, the defective recombinant thyA gene may be a non-reverting mutant gene.

As used herein, the term "non-reverting mutant" denotes that the reversion frequency may be lower than about $10^{-8}$, preferably the reversion frequency may be lower than about $10^{-10}$, even more preferably, the reversion frequency may be lower than about $10^{-12}$, even more preferably, the reversion frequency may be lower than about $10^{-14}$, most preferably, the reversion frequency may not be detectable using the routine methods known to the person skilled in the art.

In a preferred embodiment, the gene according to the invention codes for the alpha 1-antitrypsin protein, or another members of the Serpin family such as, but not limited to, antiplasmin, alpha 1-antichymotrypsin.

In a preferred embodiment, the food-grade bacterium strain according to the invention may be a *L. lactis* strain or a *Lactobacillus casei* strain or a *L. lactis* htrA strain [Poquet et al., 2000] or a *Lactobacillus plantarum* strain of a *Bifidobacterium longum* strain.

In a preferred embodiment, the food-grade bacterium strain according to the invention may be a *Lactobacillus casei* strain.

In a most preferred embodiment, the gene according to the invention codes for trappin-2.

Indeed, the inventors showed that trappin-2 may be naturally expressed in the human colonic mucosa, with a prominent expression in intestinal epithelial cells [Motta et al.] and that, patients with IBD show a down-regulation of trappin-2 in tissues compared to healthy subjects [Motta et al.].

Furthermore, the inventors have demonstrated in different models of colitis, that trappin-2 overexpression may be protective against the development of colitis (in constitutive and transient expression). Moreover, trappin-2 overexpression in models of colitis may be able to completely inhibit the increase of elastase and trypsin-like activities associated with colitis.

Finally, trappin-2 overexpression in mice may be also able to significantly inhibit colitis-induced increases of pro-inflammatory cytokines and chemokines (such as, but not limited to, IL-6, Il-17A, TNF-alpha, Interferon-gamma, MCP-1 and KC).

All these results are in favor of delivery of trappin-2 and others proteases from the WAP or Serpin family which have similar properties to treat IBD. As shown in the results below, food-grade bacteria are the most safe and efficient means to deliver this type of proteases to the gut.

In another preferred embodiment, the gene according to the invention codes for the alpha 1-antitrypsin protein.

Indeed, the alpha 1-antitrypsin protein inhibits trypsin-like activities associated with IBD (like colitis) and thus has similar effects as trappin-2.

In another preferred embodiment, the food-grade bacterium strain according to the invention may be a *Lactobacillus casei* strain which comprises a gene coding for trappin-2.

In another preferred embodiment, the food-grade bacterium strain according to the invention may be a *Lactobacillus casei* strain which comprises a gene coding for trappin-2 inserted in the thyA gene.

In another embodiment, the food-grade bacterium according to the invention is useful for the treatment of intestinal inflammatory conditions.

In another preferred embodiment, the food-grade bacterium according to the invention is useful for the treatment of an IBD and/or IBS.

The inflammatory conditions may be selected from IBD, IBS, inflammatory pulmonary disease, inflammatory articular disease or inflammatory urogenital disease.

Another object of the invention relates to a therapeutic composition comprising a food-grade bacterium according to the invention.

In a preferred embodiment, therapeutic composition according to the invention is intended for mucosal administration to a subject.

In another preferred administration, therapeutic composition according to the invention is intended for oral administration to a subject. For example, compositions may be in the form of a suspension, tablet, pill, capsule, granulate or powder.

In a liquid therapeutic composition, the food-grade bacterium according to the invention is present, free and not immobilized, in suspension. The suspension has a composition which ensures physiological conditions for a probiotic bacterium, so that in particular the osmotic pressure within the cell does not lead to lysis.

In a solid therapeutic composition, the food-grade bacterium according to the invention may be present in free, preferably lyophilized form, or in immobilized form. For example, the food-grade bacterium according to the invention may be enclosed in a gel matrix which provides protection for the cells.

A solid therapeutic composition intended for oral administration and containing the food-grade bacterium according to the invention in immobilized or non-immobilized form is preferably provided with a coating resistant to gastric juice. It is thereby ensured that the food-grade bacterium contained in the therapeutic composition may pass through the stomach unhindered and undamaged and the release of the food-grade bacterium first takes place in the upper intestinal regions.

In another aspect of the invention, the therapeutic composition contains sufficient colony-forming units (CFU) of the food-grade bacterium capable of forming the protein according to the invention so that with multiple administration of the therapeutic composition according to a patient, the state of the IBD or IBS is healed, the progression of the IBD or the IBS is stopped, and/or the symptoms of the IBD or IBS may be alleviated. According to the invention, it is in particular provided that a therapeutic composition contains about $1\times10^8$-$1\times10^{11}$, preferably about $1\times10^9$ to about $1\times10^{10}$ CFU of the food-grade bacterium according to the invention.

In a further preferred embodiment of the invention, the therapeutic composition containing the food-grade bacterium may be administered intrarectally. A rectal administration preferably takes place in the form of a suppository, enema or foam. Intrarectal administration may be particularly suitable for chronic inflammatory intestinal diseases which affect the lower intestinal sections, for example the colon. Intranasal administrations are also suitable to treat chronic pulmonary diseases such as, but not limited to, cystic fibrosis and BPCO.

In another aspect, the invention relates to a food composition comprising a food-grade bacterium according to the invention.

In a preferred embodiment, food compositions according to the invention are intended for oral administration to a subject. For example, compositions may be in the form of a suspension, tablet, pill, capsule, granulate, powder or yogurt.

In a preferred embodiment, the food composition may contain $1\times10^8$-$1\times10^{11}$, preferably $1\times10^9$-$1\times10^{10}$ CFU of the food-grade bacterium according to the invention.

In a preferred embodiment, the food composition may be administered to the patient at a daily dose of $10^{10}$ bacteria.

Although the present invention and its advantages have been described in detail, it should be understood that various changes, substitutions and alterations may be made herein without departing from the spirit and scope of the invention as defined in the appended claims.

The present invention will be further illustrated in the following Examples which are given for illustration purposes only and are not intended to limit the invention in any way.

Example

Material & Methods

Cloning of Elafin in recombinant lactic acid bacteria (*Lactococcus lactis* and *Lactobacillus casei*)

Cloning and Expression of Elafin in Lactic Acid Bacteria

Gene coding for elafin was PCR amplified from plasmid DK6-elafin. Sequences of primers used were: 5' forward Elafin (CCAATGCATCAGCAGCTGTCACGGG AGT-TCC) (SEQ ID NO: 1) and 3' reverse-Elafin (GGACTAGTCCTCACTGGGGAACGAAACA GGCC) (SEQ ID NO: 2). Primers were designed to eliminate first codons of elafin region encoding for signal peptide (SP) and was replaced by the SP of Usp45 protein ($PS_{Usp45}$), the main secreted protein from *L. lactis*. To that aim, PCR product was digested, purified, and cloned in pSEC, a *L. lactis* secretion vector. In the resulting plasmid pSEC:elafin, elafin is fused in frame with a DNA fragment encoding for RBS and $PS_{Usp45}$. Expression of the cassette is controlled by the inducible promoter $P_{nisA}$, the activity of which depends upon the concentration of nisin used. This plasmid was then introduced in a *L. lactis* strain bearing the nisin regulatory genes nisR et nisK (*L. lactis* NZ9000) to give rise the recombinant strain: NZ(pSEC:elafin). The tools used (replicons, promoter, RBS and SP) are functional in lactobacilli strains such as, but not limited to, *Lactobacillus casei* and *Lb. plantarum*. These two strains (each bearing the genes nisRK on their chromosome) have been chosen because of their persistence ability in the digestive tract (up to 4 days, as opposed to 24 to 48 hr in *L. lactis*. In addition, we have demonstrated recently that the *Lb. casei* BL23 strain possesses anti-inflammatory properties in a DSS-induced colitis model [Rochat et al, 2007]. We therefore have at our disposal non-immuno-modulatory strains weakly *L. lactis*) and strongly (*Lb. plantarum*) persistent as well as immunomodulatory strains strongly persistent (*Lb. casei*), allowing us to evaluate the feasibility of combining the intrinsic anti-inflammatory effects of the strains used with that of the molecules over-expressed.

For the induction of the $P_{nisA}$ promoter, *L. lactis* recombinant strains were cultured to $OD_{600}$=~04-0.6 and then induced with 10 μg/ml de nisin (Sigma) during 1 h. Functionality of this induction was then tested as follows: NZ (pSEC:elafin) cultures (final $OD_{600}$=~1) were separated into pellets and supernatants and content in elafin was measured by ELISA and/or Western Blot.

Animals

C57B16 mice (6-8 weeks old) were obtained from Janvier (St Quentin Fallavier) and were kept at room temperature, under 12 h light/dark cycles and having free access to food and water, except the day before the induction of colitis, where they were fasted for 12 h. All procedures were approved by Institutional animal care committee and veterinary services.

Induction of Colitis and Study Design

Colonic inflammation was induced by treatments with Dextran Sodium Sulfate (DSS). In details, DSS was dissolved in drinking water (3 or 5% wt/vol) and the animals were free to drink this solution for 7-days. Water consumption was measured in the DSS-treated groups and compared to groups of naïve mice drinking water: no difference was observed for the volume of liquid consumed, between water and DSS-drinking mice. Mice were treated daily orally, with 100 µl of $5 \cdot 10^9$ colony forming units (cfu) of wild-type, elafin-recombinant *L. lactis* or *Lb. casei*, or bacterial medium alone. The first treatment started at the same time DSS was added to drinking water and the last treatment was on the day of the sacrifice (day 7). Body weight and survival rate were measured daily after the induction of colitis. On day 7 after adding DSS to their drinking water, mice were sacrificed and colons were harvested for measure of several parameters of inflammation: macroscopic score, bowel thickness, myeloperoxydase (MPO) activity, proteolytic activity, cytokine expression.

Measure of Inflammatory Parameters

Macroscopic damage was evaluated as follows. Briefly, when observed, the following parameters were given a score of 1: haemorrhage, edema, stricture, ulceration, fecal blood, mucus, and diarrhoea. Erythema was scored a maximum of 2 depending on the length of the area being affected (0: absent, 1: less than 1 cm, 2: more than 1 cm). Adhesion was scored based on its severity (0: absent, 1: moderate, 2: severe).

MPO was measured as an index of granulocyte infiltration in colonic tissues harvested at the time of the sacrifice. Tissue samples were homogenized in a solution of 0.5% hexadecyltrimethylamonium bromide in phosphate buffer (pH 6), and centrifuged at 13 000×G for 2 min. Supernatants were added to a buffer containing 1% hydrogen peroxide and 0-dianisidine dihydrochloride. Optical density readings for the enzymatic solution were read for 2 min at 450 nm.

For cytokine and chemokine protein measures, frozen colonic samples harvested at sacrifice were homogenized using a polytron for 30 s at 4° C. in 500 µl of cell lysis buffer (20 mM Tris-Hcl, pH 7.5, 150 mM NaCl, 1 mM $Na_2EDTA$, 1 mM EGTA, 1% Triton X-100, 2.5 mM sodium pyrophosphate, 1 mM beta-glycerophosphate, 1 mM $Na_3VO_4$, 1 µg/ml leupeptin; Cell Signalling, Sigma) supplemented with anti-proteases (Roche Diagnostics, Meylan, France) cocktail. After centrifugation (10 000×g, 10 min, 4° C.), supernatants were filtered on QIAshredder columns (Qiagen, France) and fifty microliters of this homogenate was used for simultaneous dosage of cytokines and chemokines using cytometric bead array on fluorescent cell sorter FACSCalibur. Raw values were normalized to tissue weight (average from 30 to 50 mg) and cytokine concentrations were extrapolated from standard curves with the help of FCAP Array® software. In accordance with the manufacturer's information, only values above the limit of cytokine detection were considered.

Serine Protease Activity in Colonic Tissues and Luminal Washes

Upon sacrifice, the entire colon was excised and 1 ml PBS was instilled and washed twice through the lumen. Proteolytic activities (trypsin-like and elastase activity) were measured both in those lumenal washes. Trypsin-like and elastase-like activities were measured using tosyl-Gly-Pro-Arg-p-nitroanilide (150 µM, Sigma) and MeO-succinyl-Ala-Ala-Pro-Val-p-nitroanilide (SEQ ID NO: 3) (100 µM, Sigma, Saint Quentin Fallavier, France) respectively as substrates. Samples (20 µl for trypsin activity or 10 µl for elastase activity) were re-suspended in their respective buffer: 100 mM Tris/HCl, 1 mM $CaCl_2$, pH=8 for trypsin activity and 50 mM Tris-HCl, 500 mM NaCl, 0.1% Triton X100 for elastase activity. The change in absorbance at 405 nm was determined over 30 minutes at 37° C. with a microplate reader NOVOstar™ (BMG Labtech, France). Activity was compared to known standard dilution of trypsin from porcine pancreas (Sigma) or human neutrophil elastase (Sigma). Protein concentration in the lumenal washes was determined using colorimetric dosage of bicinchoninic acid on microplate (BCA Kit®, Pierce, Thermo Scientific, Courtaboeuf, France) and was used to standardize the proteolytic activity in each samples.

Induction and Measure of Visceral Pain Behaviors in Response to Mustard Oil

Cultures of the *L. lactis* three strains of (*L. lactis* wt, *L. lactis*-Elafin, *L. lactis*-IL-10) were performed in M17 medium (Oxoid) supplemented with glucose (0.5%) supplemented with Chloramphenicol (10 µg/mL) at 30° C. without shaking Bacteria from overnight cultures were grown in fresh medium at 1/50 (v/v) until $OD_{600}$=0.4 to 0.6. Bacteria were then cultured for one more hr with Nisin (1 ng/mL), added to enable recombinant protein expression. Bacteria were harvested by centrifugation at 450 g and washed with sterile PBS. The pellets were resuspended in sterile PBS at a final concentration of $5 \times 10^{10}$ cfu/mL. Groups of 4 to 8 mice were treated daily with 100 µL ($5 \times 10^9$ cfu) of bacterial suspension by intragastric administration for seven days. At day 8, mice were administered with 50 µL of PBS or mustard oil (0.01% (v/v) in ethanol 70%) by intracolonic instillation, performed under slight isoflurane anesthesia. The number of pain-related behavioral responses (abdominal retractions, licking of the abdomen, stretching, and squashing of the lower abdomen against the floor) were then counted for 20 min.

Statistics

Comparisons among groups were made using a 2-tailed Student's t test with Bonferroni correction. Data are expressed as mean±SEM, and a P value less than 0.05 was considered significant.

Results

Recombinant *Lactococcus lactis* Expressing Elafin Protects Against the Development of DSS Colitis in Mice As expected, DSS-induced colitis (5% DSS) caused severe weight loss in all groups of mice compared to control mice that drank water. None of the lactic acid bacteria treatments significantly modified this weight loss (FIG. 1A). DSS in drinking water also caused macroscopic damage, increased wall thickness and increased MPO activity in colonic tissues (FIGS. 1 B, C, D). Mice that were treated with wild-type *L. lactis* did not show significant decrease in colonic wall thickness and MPO activity, only a slight decrease in macroscopic damage score was observed in that group, compared to DSS alone-treated mice. In contrast, mice treated with recombinant *L. lactis* expressing elafin showed after the induction of DSS colitis a significantly reduced macroscopic damage score and significant less increase in colonic wall thickness, but MPO activity was not different from DSS alone group (FIGS. 1B, C, D). In addition, mice treated with recombinant *L. lactis* expressing IL-10 cytokine showed reduced macroscopic damage score and MPO activity after the induction of DSS colitis, but wall thickness was not modified by this treatment compared to DSS alone (FIGS. 1B, C, D). In non-inflamed mice, none of the treatments modified the inflammatory parameters compared to naïve control mice.

DSS-induced increase in trypsin-like activity was significantly reduced in mice treated with recombinant *L. lactis* expressing Elafin, but was not changed in mice treated with wild-type *L. lactis* or recombinant *L. lactis* expressing IL-10 (FIG. 2A). Only treatment with recombinant *L. lactis* expressing elafin was able to significantly reduce DSS-induced increase in elastase activity (FIG. 2B).

Figure 3:
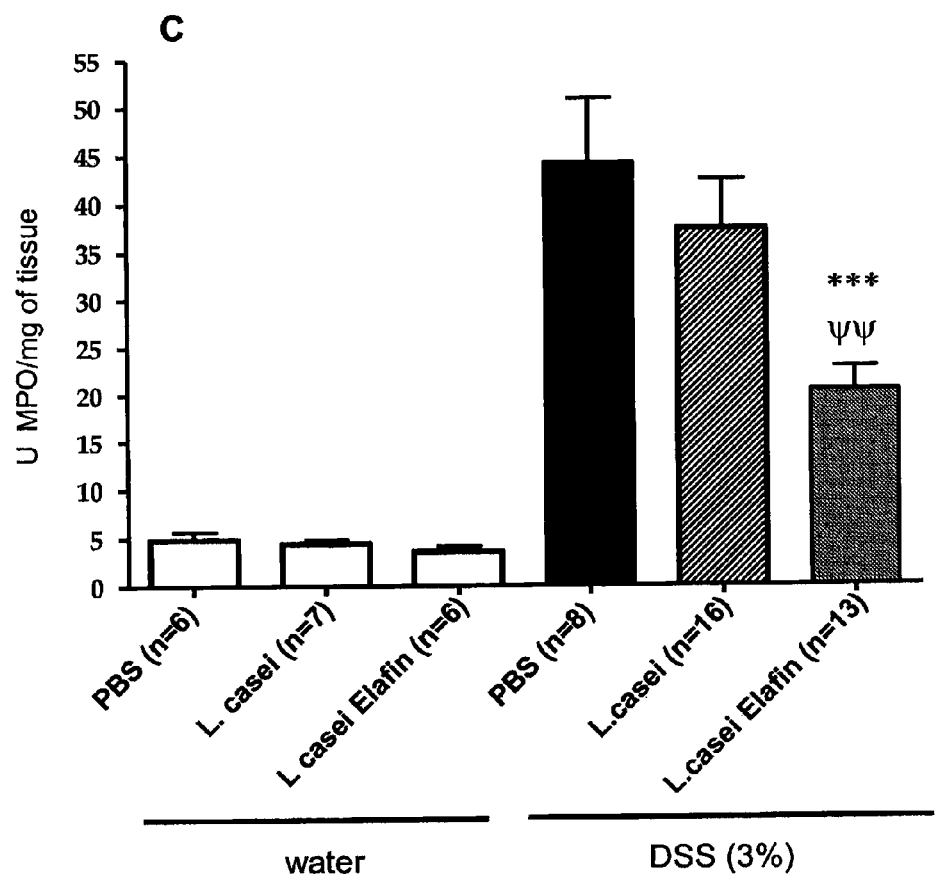
FIGS. 3A-C: Macroscopic score (A), Wall thickness (B), and myeloperoxydase (MPO) activity (C) in colonic tissues from mice that had water or water+DSS (3%) in their dinking bottles, and that received daily oral treatments for 7-days with wild-type *Lb. casei*, or recombinant *Lb. casei* strains expressing Elafin. Significant differences compared to PBS-treated mice that have received DSS were noted * for p<0.05,  for p<0.01, and * for p<0.005. Significant differences compared to wild-type *Lb. casei*-treated mice were noted Ψ for p<0.05, ΨΨ for p<0.01, and ΨΨΨ for p<0.005.

Recombinant *Lactobacillus casei* Expressing Either Elafin Protects Against the Development of DSS Colitis in Mice While mouse treatment with wild-type *Lb. casei* significantly reduced the macroscopic scores observed after the induction of DSS colitis, this treatment failed to reduce the increased wall thickness and MPO activity compared to DSS alone (FIGS. 3 A, B, C). In contrast, treatments with recombinant *Lb. casei* expressing elafin significantly reduced all parameters of inflammation: macroscopic damage score, colonic wall thickness and MPO activity (FIGS. 3A, B, C).

DSS-induced increase in trypsin-like activity was significantly reduced in mice treated with recombinant *Lb. casei* expressing Elafin, compared to mice treated with wild-type *Lb. casei* (FIG. 4A). The level of elastase activity was also significantly reduced in mice with colitis (DSS) treated with recombinant *Lb. casei* expressing elafin, compared to inflamed (colitis) mice treated with wild-type *Lb. casei*, or even compared to inflamed mice treated with PBS (FIG. 4B).

Protein expression of the chemokine RANTES was not significantly increased by DSS colitis at the observed time-point (7-days after the start of DSS treatment). Wild-type or Elafin-secreting *Lb. casei* failed to modify the level of RANTES expression in DSS-treated mice (FIG. 5 A). TNFα, IL-6, MCP1, KC, INFγ and IL-17A were all significantly increased by DSS colitis, 7 days after its induction (FIGS. 5B to G). Treatment of mice with recombinant *Lb. casei* expressing elafin significantly reduced protein expression of IL-6, MCP1, KC and IL-17 (FIGS. 5C, D, E, G), but failed to reduce the level of expression of other pro-inflammatory cytokines such as TNFα and INFγ (FIGS. 5B and F). Interestingly, while DSS colitis did not cause any increase in the cytokines IL-2, IL-4, IL-5, IL-10 and IL-13 (FIGS. 6 A to E), treatment of mice with *Lb. casei* recombinant for elafin raised significantly the expression of those cytokines, but only in a colitis context (after DSS treatment). This increase in Th2 cytokines in response to *Lb. casei* recombinant for elafin, could explain, at least in part, the anti-inflammatory effects of this recombinant bacteria. Levels of IL2, IL-4, IL-5, IL-10 and IL-13 were not modified by any of the other treatments in either inflamed (DSS) or non-inflamed mice (FIGS. 6 A to E).

Recombinant *Lactococcus lactis* for the Expression of Elafin Decrease Visceral Pain Behavior Intracolonic administration of mustard oil caused a significant increase in the number of pain behaviors: both the number of abdominal retractions and the number of integrated pain behaviors such as licking, stretching, and squashing against the floor (FIGS. 7 A and B). Considering all behaviors together, treatment with wild-type, IL-10 recombinant or elafin-secreting *L. lactis* had no effect (FIG. 7A). When considering only the integrated pain behaviors, elafin-, but not IL-10-recombinant *L. lactis* or wild-type significantly reduced the number of pain behaviors (FIG. 7B). Moreover, only recombinant *L. lactis* expressing elafin induced a notable decrease in the number of pain behaviors compared both to PBS treatment or wild-type *L. lactis* treatment (FIG. 7B).

Results with the htrA Strain

Figure 8:
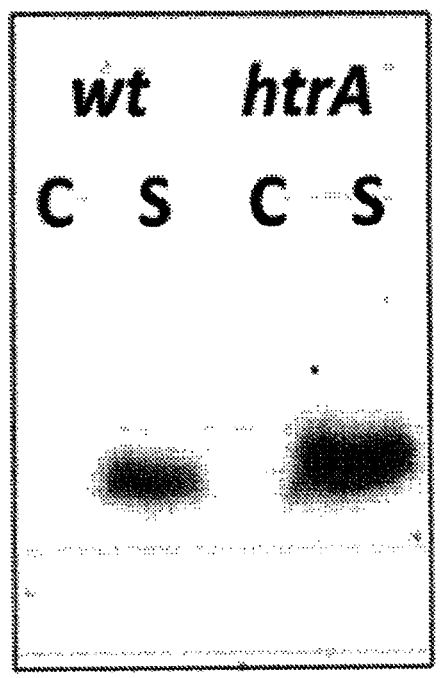
FIG. 8: Elafin secreted by *L. lactis* wt and htrA strains. Western blot experiments performed with antibodies anti-elafin on cellular (C) and supernatant (S) extracts of wild type (wt) or htrA (htrA) strains. Elafin production was induced by nisin from exponential-phase cultures of wt or htrA strains (both containing the expression vector where elafin gene expression may be induced by nisin addition).

*L. lactis* expresses only one housekeeping extracellular protease called htrA which degrades all the unfolded exported proteins [Poquet et al, 2000 and U.S. Pat. No. 6,994,997 and FR2787810]. A *L. lactis* mutant strain inactivated in htrA gene was constructed and allowed increasing the production rate of several heterologous secreted proteins in *L. lactis* [Poquet et al, 2000 and Miyoshi et al, 2002]. According to the invention, the elafin expression cassette was cloned in the htrA mutant. Elafin production levels in the htrA mutant and in the wild type (wt) strain were compared by Western blot experiments (FIG. 8). A significant increase of secreted elafin was observed in the supernatant of the htrA mutant compared to the wt strain. Thus, the htrA strain will allow higher production and secretion levels of elafin.

Figure 9:
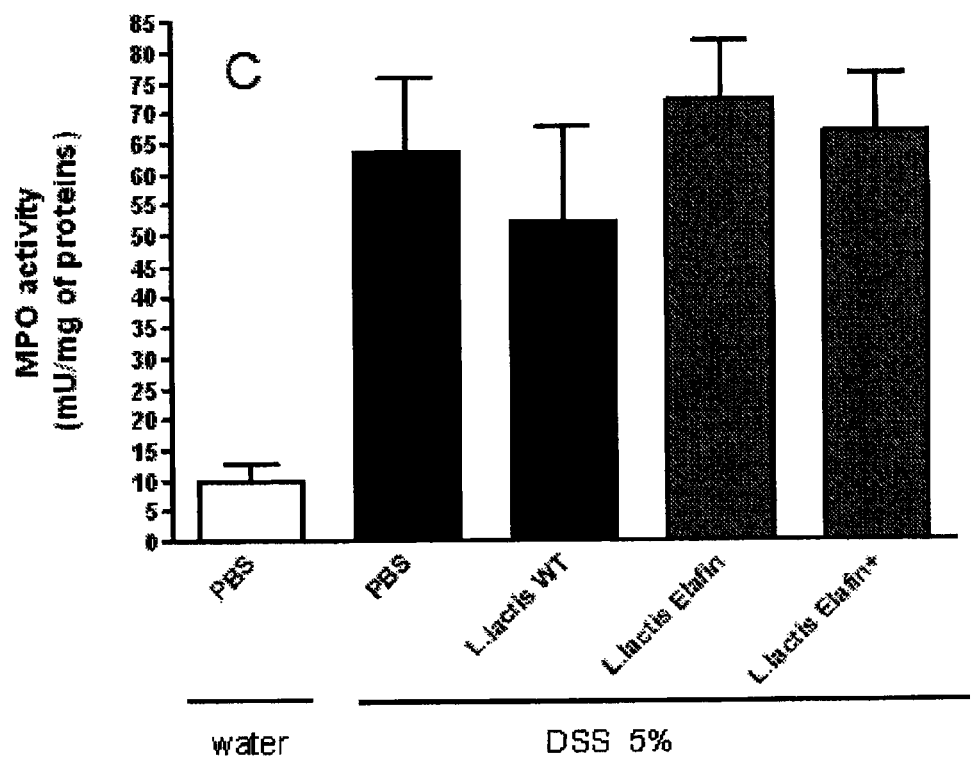
FIGS. 9A-C: Protective effects of *L. lactis* wt and htrA mutant strains in DSS 5%-induced colitis model. Macroscopic (A), histological damages (B) and MPO activities (C) were evaluated in different groups of 10 mice treated either with water (negative control) or with DSS 5%. Two first control groups were treated i) with water and orally fed with PBS (negative control group) and ii) with DSS 5% and orally fed with PBS (positive control group). The other groups were all treated with DSS 5% and with either wt strain (WT), wt strain expressing elafin (Elafin) and htrA mutant strain expressing elafin (Elafin+).

These two strains were then tested in DSS-induced colitis model and we confirmed in vivo that the htrA mutant protects the mice against the colitis damages better than the wt strain (FIGS. 9 A, B and C).

Comparative Results

Figure 10:
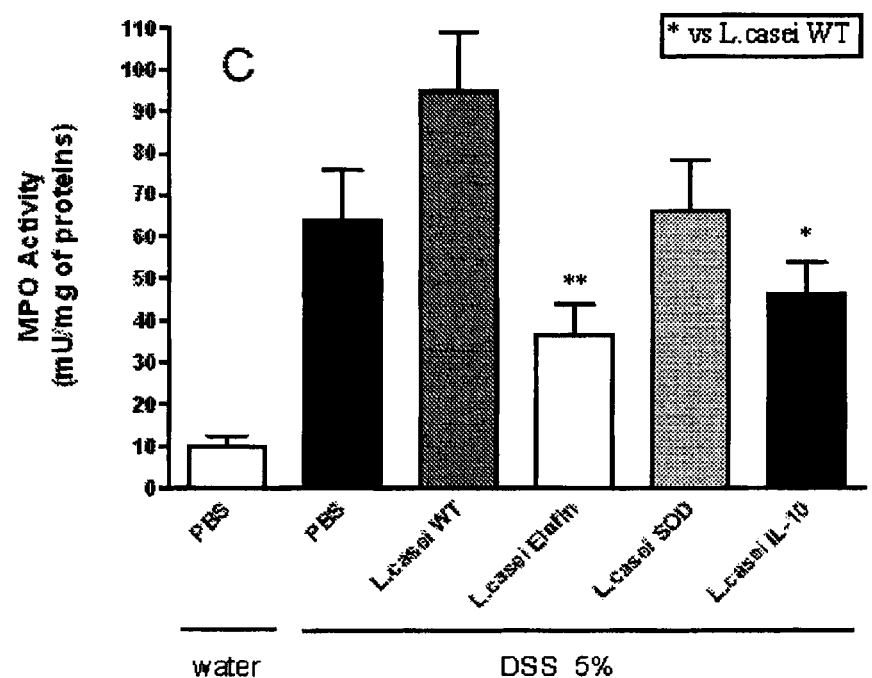

The protective effects of IL-10, superoxide dismutase (SOD) and elafin-producing *L. casei* strains were evaluated in parallel in DSS 5%-induced colitis model. It should be reminded that *L. casei* possesses two major differences compared to *L. lactis*: i) higher persistence in the GIT and ii) intrinsic anti-inflammatory properties [Rochat et al, 2007; Watterlot et al, 2010]. As shown in FIGS. 10A, B and C, the best protective effects on the three criteria (macroscopic, histological and MPO activity) are obtained with Elafin-producing *L. casei* strain followed by SOD-producing *L. casei* strain. *L. casei* strain producing IL-10 provided only poor effects.

Moreover, elafin-producing *L. casei* strain afforded a better protection than the two *L. lactis* strains (wt *L. Lactis* and htrA strain) (FIG. 11).

These results are most surprising considering the fact that elafin possesses in vitro and in vivo antibacterial activities [Simpson A J et al., 1999]. Accordingly, the skilled person would have expected a poor or no production at all by the bacterium host. On the contrary, the results obtained by the inventors show a very good production of elafin by the probiotic and hence a therapeutic effect.

Moreover, both in vitro and in vivo studies (including clinical studies) showed that the lack of the host antimicrobial shield is potentially deleterious in colonic diseases [Salzman N H et al., 2003 and Bevins C L et al., 2009].

Thus, the pleiotropic anti-microbial/anti-inflammatory activity of elafin makes it a very good therapeutic molecule candidate as compared to IL-10.

EDTA Induction of Promoter Zinc (PZn) zitR-Controlled Expression in *L. lactis*.

Production of elafin in *L. lactis* driven by PZn zitR [Llull D and Poquet I. 2004] was tested by Western blot analysis after 1 h of induction with 1 mM of EDTA. Non-induced cultures samples, cellular pellet (C) and supernatant (S), produce very low levels and secretion of elafin while induced cultures result in higher levels of expression and secretion (FIG. 12).

REFERENCES

Throughout this application, various references describe the state of the art to which this invention pertains. The disclosures of these references are hereby incorporated by reference into the present disclosure.

Bevins C L, Stange E F, Wehkamp J. Decreased Paneth cell defensin expression in ileal Crohn's disease is independent of inflammation, but linked to the NOD2 1007fs genotype. Gut. 2009 June; 58(6):882-3.

Braat, H., M. P. Peppelenbosch, and D. W. Hommes. 2003. Interleukin-10-based therapy for inflammatory bowel disease. Expert. Opin. Biol. Ther. 3:725-731.

Braat, H., P. Rottiers, D. W. Hommes, N. Huyghebaert, E. Remaut, J. P. Remon, S. J. van Deventer, S. Neirynck, M. P. Peppelenbosch, and L. Steidler. 2006. A phase I trial with transgenic bacteria expressing interleukin-10 in Crohn's disease. Clin. Gastroenterol. Hepatol. 4:754-759.

Bron Peter A., Marcos G. Benchimol, Jolanda Lambert, Emmanuelle Palumbo, Marie Deghorain, Jean Delcour, Willem M. de Vos, Michiel Kleerebezem, and Pascal Hols. Use of the alr Gene as a Food-Grade Selection Marker in Lactic Acid Bacteria. Environmental Microbiology, November 2002, p. 5663-5670.

Cenac, N., C. N. Andrews, M. Holzhausen, K. Chapman, G. Cottrell, P. Andrade-Gordon, M. Steinhoff, G. Barbara, P. Beck, N. W. Bunnett, K. A. Sharkey, J. G. Ferraz, E. Shaffer, and N. Vergnolle. 2007. Role for protease activity in visceral pain in irritable bowel syndrome. J. Clin. Invest 117:636-647.

Hedin, C., K. Whelan, and J. O. Lindsay. 2007. Evidence for the use of probiotics and prebiotics in inflammatory bowel disease: a review of clinical trials. Proc. Nutr. Soc. 66:307-315. Sallenave, J.-M. Biol. Chem. Hoppe-Seyler 372 (1991), pp. 13-21.

Hyun, E., P. Andrade-Gordon, M. Steinhoff, and N. Vergnolle. 2008. Protease-activated receptor-2 activation: a major actor in intestinal inflammation. Gut 57:1222-1229.

Llull D. and I. Poquet. New Expression System Tightly Controlled by Zinc Availability in *Lactococcus lactis*. Environmental Microbiology, September 2004, p. 5398-5406.

Motta Jean-Paul, Laurent Magne, Delphyne Descamps, Corinne Rolland, Camila Squarzoni-Dale, Perrine Rousset, Laurence Martin, Nicolas Cenac, Viviane Balloy, Michel Huerre, Dieter Jenne, Julien Wartelle, Azzaq Belaaouaj, Emmanuel Masl, Jean-Pierre Vinel, Laurent Alric, Michel Chignard, Nathalie Vergnolle, Jean-Michel Sallenave. Modifying the protease, anti-protease pattern by elafin over-expression protects mice from colitis. Gastroenterology 2011, In Press.

Poquet I, Saint V, Seznec E, Simoes N, Bolotin A, Gruss A. HtrA is the unique surface housekeeping protease in *Lactococcus lactis* and is required for natural protein processing. Mol Microbiol. 2000 March; 35(5):1042-51.

Sallenave J.-M, Silva A., Marsden M. E. and Ryle A. P. Am. J. Respir. Cell Mol. Biol. 8 (1993), pp. 126-133.

Sallenave J M. Secretory leukocyte protease inhibitor and elafin/trappin-2: versatile mucosal antimicrobials and regulators of immunity. Am J Respir Cell Mol Biol. 2010 June; 42(6):635-43. Epub 2010 Apr. 15. Review.

Sartor, R. B. 2004. Therapeutic manipulation of the enteric microflora in inflammatory bowel diseases: antibiotics, probiotics, and prebiotics. Gastroenterology 126:1620-1633.

Salzman N H, Ghosh D, Huttner K M, Paterson Y, Bevins C L. Protection against enteric salmonellosis in transgenic mice expressing a human intestinal defensin. Nature. 2003 Apr. 3; 422(6931):522-6.

Simpson A J, Maxwell A I, Govan J R, Haslett C, Sallenave J M. Elgin (elastase-specific inhibitor) has anti-microbial activity against gram-positive and gram-negative respiratory pathogens. FEBS Lett. 1999 Jun. 11; 452(3):309-13.

Steidler, L., W. Hans, L. Schotte, S. Neirynck, F. Obermeier, W. Falk, W. Fiers, and E. Remaut. 2000. Treatment of murine colitis by *Lactococcus lactis* secreting interleukin-10. Science 289:1352-1355.

Thierry Moreau, Kevin Baranger, Sebastien Dade, Sandrine Dallet-Choisy, Nicolas Guyot, Marie-Louise Zani. Multifaceted roles of human elafin and secretory leukocyte proteinase inhibitor (SLPI), two serine protease inhibitors of the chelonianin family. Biochimie 90 (2008) 284e295.

Vergnolle, N. 2005. Clinical relevance of proteinase-activated receptors in the gut. Gut 54:867-874.

Vergnolle, N., L. Cellars, A. Mencarelli, G. Rizzo, S. Swaminathan, P. Beck, M. Steinhoff, P. Andrade-Gordon, N. W. Bunnett, M. D. Hollenberg, J. L. Wallace, G. Cirino, and S. Fiorucci. 2004. A role for proteinase-activated receptor-1 in inflammatory bowel diseases. J Clin Invest 114:1444-1456.

The invention is further described by the following numbered paragraphs:

1. A molecule selected from the trappin-2 protein or an active fraction of the trappin-2 protein, a member of the WAP family proteins or an active fraction of a member of the WAP family proteins or a member of the Serpin family or an active fraction of a member of the Serpin family for the treatment of Irritable Bowel Syndrome (IBS).

2. A molecule according to the paragraph 1 expressed by a host cell genetically engineered.

3. A recombinant food-grade bacterium comprising a gene selected from a gene coding for the trappin-2 protein or an active fraction of the trappin-2 protein, a gene coding for a member of the WAP family proteins or an active fraction of a member of the WAP family proteins or a gene coding for a member of the Serpin family proteins or an active fraction of a member of the Serpin family proteins.

4. A bacterium according to paragraph 3 wherein the food-grade bacterium is a probiotic bacterium.

5. A probiotic bacterium according to paragraph 3 or 4 wherein the bacterium comprises a defective auxotrophic gene, whereby survival of said bacterium is strictly dependent upon the presence of specific compounds.

6. A probiotic bacterium according to paragraph 5 wherein the defective auxotrophic gene is the thyA gene.

7. A probiotic bacterium according to paragraph 4 wherein the selected gene is inserting in the thyA gene.

8. A probiotic bacterium according to any one of paragraphs 3 to 5 wherein the gene coding for the WAP or Serpin family progene is trappin-2 or the alpha I-antitrypsin protein.

9. A food-grade bacterium according to any one of paragraph 3 to 6 selected from *Lactococcus lactis, Lactobacillus casei, Lactobacillus plantarum*.

10. A food-grade bacterium according to any one of paragraphs 3 to 9 for the treatment of an inflammatory condition.

11. A food-grade bacterium according to paragraph 10 wherein the inflammatory condition is selected from Inflammatory Bowel Disease, Irritable Bowel Syndrome, inflammatory pulmonary disease, inflammatory articular disease or inflammatory urogenital disease.

12. A therapeutic composition comprising a food-grade bacterium according to any one of paragraphs 3 to 9.

13. A food composition comprising a food-grade bacterium according to any one of paragraphs 3 to 9.

14. A composition according to any one of paragraphs 10 and 11 wherein the composition is intended for oral administration to a subject.

21. A molecule selected from the trappin-2 protein or an active fraction of the trappin-2 protein, a member of the WAP Serpin family proteins or an active fraction of a member of the WAP family proteins or a member of the Serpin family or an active fraction of a member of the Serpin family for the treatment of Irritable Bowel Syndrome (IBS).

22. A molecule according to the paragraph 21 expressed by a genetically engineered host cell.

23. A recombinant food-grade bacterium comprising a recombinant gene selected from a gene coding for the trappin-2 protein or an active fraction of the trappin-2 protein, a gene coding for a member of the WAP family proteins or an active fraction of a member of the WAP family proteins or a gene coding for a member of the Serpin family proteins or an active fraction of a member of the Serpin family proteins.

24. A bacterium according to paragraph 23 wherein the food-grade bacterium is a probiotic bacterium.

25. A probiotic bacterium according to paragraph 23 or 24 wherein the bacterium comprises a defective auxotrophic gene, whereby survival of said bacterium is strictly dependent upon the presence of specific compounds.

26. A probiotic bacterium according to paragraph 25 wherein the defective auxotrophic gene is selected from the thyA gene or the alr gene.

27. A probiotic bacterium according to paragraph 25 wherein the selected gene is inserted in place of the defective auxotrophic gene.

28. A probiotic bacterium according to any one of paragraphs 23 to 25 wherein the gene coding for the WAP or Serpin family protein encodes the trappin-2 protein or the alpha 1-antitrypsin protein.

29. A food-grade bacterium according to any one of paragraphs 23 to 26 selected from Lactic Acid Bacterium, *Bifidobacterium, Lactococcus* or *Lactobacillus*.

30. A food-grade bacterium according to any one of paragraphs 23 to 26 selected from *Lactococcus lactis, Lactococcus lactis* htrA, *Lactobacillus casei, Lactobacillus plantarum,* and *Bifidobacterium longum*.

31. A food-grade bacterium according to any one of paragraphs 23 to 30 for the treatment of an inflammatory condition.

32. A food-grade bacterium according to paragraph 31 wherein the inflammatory condition is selected from Inflammatory Bowel Disease, Irritable Bowel Syndrome, inflammatory pulmonary disease, inflammatory articular disease or inflammatory urogenital disease.

33. A therapeutic composition comprising a food-grade bacterium according to any one of paragraphs 23 to 30.

34. A therapeutic composition according to paragraph 33, wherein the composition is intended for mucosal, oral, intranasal or rectal administration to a subject.

35. A therapeutic composition according to paragraph 31 or 32, wherein the composition is intended for mucosal, oral, intranasal or rectal administration to a subject.

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

What is claimed is:

1. A recombinant food-grade *Lactobacillus casei* bacterium consisting essentially of a recombinant gene comprising a nucleic acid sequence encoding (a) a signal peptide of Usp45 protein and (b) the active fraction of the elafin protein, wherein the recombinant bacterium expresses and secretes the active fraction of the elafin protein, and wherein the active fraction exhibits trypsin-like and elastase-like activity.

2. The recombinant food-grade *Lactobacillus casei* bacterium of claim 1, wherein the bacterium comprises a defective thyA auxotrophic gene.

3. The recombinant food-grade *Lactobacillus casei* bacterium of claim 2, wherein the said recombinant gene is inserted in the defective auxotrophic gene.

4. A therapeutic composition comprising the food grade *Lactobacillus casei* bacterium according to claim 1, 2 or 3.

5. A food composition comprising the food-grade *Lactobacillus casei* bacterium according to claim 1, 2 or 3.

6. The recombinant food-grade *Lactobacillus casei* bacterium of claim 1, wherein the recombinant gene coding for said active fraction of the elafin protein has the sequence of a product obtained by PCR amplification of a plasmid encoding the elafin gene, wherein the PCR amplification utilizes a 5' forward-Elafin primer having the sequence according to SEQ ID NO: 1, and a 3' reverse-Elafin primer having the sequence according to SEQ ID NO: 2.

* * * * *

SEQUENCE LISTING

```
<160> NUMBER OF SEQ ID NOS: 3

<210> SEQ ID NO 1
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
ccaatgcatc agcagctgtc acgggagttc c                                31

<210> SEQ ID NO 2
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
ggactagtcc tcactgggga acgaaacagg cc                               32

<210> SEQ ID NO 3
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
```

```
<222> LOCATION: (1)..(1)
<223> OTHER INFORMATION: MeO-succinyl-Ala
<220> FEATURE:
<221> NAME/KEY: MOD_RES
<222> LOCATION: (4)..(4)
<223> OTHER INFORMATION: Val-p-nitroanilide

<400> SEQUENCE: 3

Ala Ala Pro Val
1
```